United States Patent
Lubisch et al.

[11] Patent Number: 5,849,744
[45] Date of Patent: Dec. 15, 1998

[54] PYRROLYL TETRAHYDROBENZOQUINOXALINE DIONES, THEIR PREPARATION AND USE AS GLUTAMATE RECEPTOR ANTAGONIST

[75] Inventors: Wilfried Lubisch, Mannheim; Michael Vierling, Dannstadt-Schauernheim; Berthold Behl; Hans Peter Hofmann, both of Limburgerhof, all of Germany

[73] Assignee: BASF Aktiengesellschaft, Ludwigshafen, Germany

[21] Appl. No.: 809,697

[22] PCT Filed: Oct. 2, 1995

[86] PCT No.: PCT/EP95/03902

§ 371 Date: Mar. 27, 1997

§ 102(e) Date: Mar. 27, 1997

[87] PCT Pub. No.: WO90/11922

PCT Pub. Date: Apr. 25, 1996

[30] Foreign Application Priority Data

Oct. 14, 1994 [DE] Germany .................... 44 36 852.6

[51] Int. Cl.⁶ .................... A61K 31/495; C07D 403/04
[52] U.S. Cl. ............................. 514/250; 544/349
[58] Field of Search ................ 544/344; 514/250

[56] References Cited

U.S. PATENT DOCUMENTS 5,721,234  2/1998  Bigge et al. ................ 514/250

FOREIGN PATENT DOCUMENTS

| | | |
|---|---|---|
| 39887/93 | 12/1993 | Australia . |
| 260 467 | 3/1988 | European Pat. Off. . |
| 283 959 | 9/1988 | European Pat. Off. . |
| 315 959 | 5/1989 | European Pat. Off. . |
| 374 534 | 6/1990 | European Pat. Off. . |
| 377 112 | 7/1990 | European Pat. Off. . |
| 566 393 | 8/1993 | European Pat. Off. . |
| 572 852 | 12/1993 | European Pat. Off. . |
| 41 35 871 | 4/1993 | Germany . |
| 91/13878 | 9/1991 | WIPO . |
| 92/07847 | 5/1992 | WIPO . |

OTHER PUBLICATIONS

Bigge et al, *Chemical Abstracts*, vol. 125, No. 114711 (Abstract fr WO 96 17832), (1996).
Lees, *Pharmacology and Patholphysiology*, 5, pp. 51–74, (1996).
Doble, *Therapie*, 50, pp. 319–337, (1995).
Lipton, *Tins*, 16, pp. 527–532, (1993).
Schousboe et al, Abstract for Clin. Neurosci. 4 pp. 194–198 (1997).
Bioorganic & Medicinal Chem. Lts., vol. 3, No. 12, pp. 2801–2804, 1993, Synthesis and Excitatory Amino . . . , Epperson et al.

*Primary Examiner*—Emily Bernhardt
*Attorney, Agent, or Firm*—Keil & Weinkauf

[57] ABSTRACT

Pyrrolyltetrahydrobenzoquinoxalinediones of the formula I

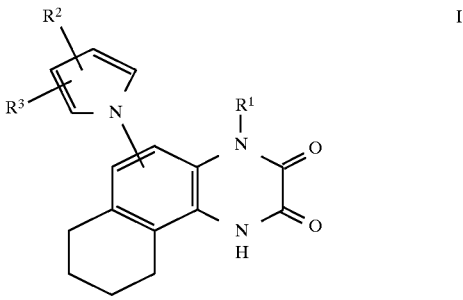

and their tautomeric and isomeric forms, and their physiologically tolerated salts, in which the variables have the meanings stated in the description, and the preparation thereof are described. The novel compounds are antagonists of the glutamate receptor subtypes and are thus suitable for controlling various diseases.

4 Claims, No Drawings

PYRROLYL TETRAHYDROBENZOQUINOXALINE DIONES, THEIR PREPARATION AND USE AS GLUTAMATE RECEPTOR ANTAGONIST

The present invention relates to novel pyrrolyltetrahydrobenzoquinoxalinediones, processes for the preparation thereof and the use thereof for controlling diseases.

Excitatory amino acids, in particular glutamate, are widespread in the central nervous system. The excitatory amino acid glutamate acts as transmitter substance for receptors of which various subtypes are known. One subtype is called, for example, the NMDA receptor after the specific agonist N-methyl-D-aspartate. This NMDA receptor has various binding sites for agonists and antagonists. The amino acid glycine likewise binds to the NMDA receptor and modulates the effect of the natural agonist glutamic acid. Antagonists on this glycine binding site may accordingly show antagonistic effects on the NMDA receptor and inhibit an overexcitation of this receptor.

Two other subtypes of glutamate receptors are the AMPA receptor and the kainate receptor which are each called after the specific agonists 2-amino-3-hydroxy-5-methyl-4-isoxazolepropionic acid (AMPA) and kainic acid. In a similar way to the NMDA receptor already mentioned, antagonists of these receptors could likewise inhibit overexcitation.

Elevated glutamate levels occur in a number of neurodegenerative disorders or psychological disturbances and may lead to states of overexcitation or toxic effects in the CNS.

Antagonists of the glutamate receptor subtypes can thus be used to treat these disorders. Glutamate antagonists, which include, in particular, NMDA antagonists, and their modulators (such as glycine antagonists) and the AMPA antagonists, are suitable for therapeutic use as remedies for neurodegenerative disorders (Huntington's chorea and Parkinson's diseases), neurotoxic disturbances following hypoxia, anoxia or ischemia, as occur after stroke, or else as antiepileptics, antidepressants and anxiolytics (cf. Arzneim. Forschung 40 (1990) 511–514; TIPS, 11 (1990) 334–338 and Drugs of the Future 14 (1989) 1059–1071).

Derivatives of quinoxaline-2,3(1H,4H)-dione II

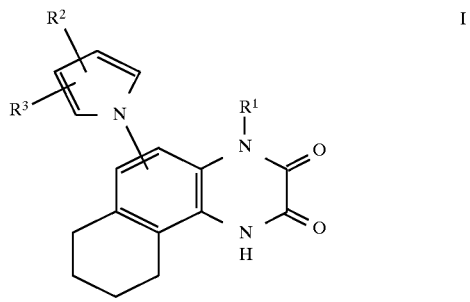

have been described in several publications (EP 374 534 and EP 260 467) as glutamate antagonists. Many of the known derivatives are unsubstituted in the heterocyclic quinoxaline fragment (II, $R^1$, $R^2$=hydrogen). However, some derivatives in which $R^1$ in II is not hydrogen are also known. Thus, EP 377 112 and EP 374 534 have mentioned N-hydroxyquinoxalines (II; $R^1$=$OR^4$). EP 315 959, DE 4 135 871, WO 91/13 878 and WO 92/07 847 described alkyl radicals as $R^1$ in II, it also being possible for the alkyl chain to be substituted by acids, esters or amides. Likewise, alkyl acids (=$R^1$) are mentioned in Bioorg. & Med. Chemistry Lett. 3 (1993) 2801–4.

N-Hydroxyquinoxalinediones (II, $R^1$=OH) or O-alkylated derivatives have been described in EP 374 534 and EP 377 112. In EP 374 534 there was also synthesis of a N-hydroxytetrahydrobenzoquinoxalinedione (Example 5). Unsubstituted tetrahydrobenzoquinoxalinediones (II, $R^1$=$R^2$=H) were claimed in EP 283 959. Tetrahydrobenzoquinoxalinediones which carry a substituted alkyl radical in $R^1$ or $R^2$ have never been described to date.

Quinoxalinedione derivatives II which carry a heterocycle as substituent $R^3$ have likewise been disclosed. Thus, EP 556 393 mentions imidazoles, triazoles and pyrazoles. Pyrroles (II, with $R^3$=pyrrolyl) have been described as glutamate antagonists in EP 572 852.

The invention relates to novel pyrrolyltetrahydrobenzoquinoxalinediones of the formula I

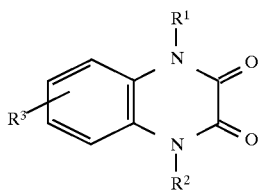

and their tautomeric and isomeric forms, and their physiologically tolerated salts, in which the variables have the following meanings:

$R^1$ hydrogen; an aliphatic radical which has 1 to 6 carbon atoms and can carry one or two different substituents of the formulae —$COOR^4$, —$CONHR^4$, —CO—$R^4$, —$OR^4$, —$NHR^4$, —NH—CO—$R^4$, —CONH—$SO_2R^4$ or $NHSO_2R^4$ where $R^4$ is hydrogen, $C_1$–$C_4$-alkyl, phenyl, benzyl, 1-phenylethyl or 2-phenylethyl, where the phenyl rings in $R^4$ can be substituted by 1, 2 or 3 of the following substituents: $C_1$–$C_4$-alkyl, $CF_3$, $C_1$–$C_4$-alkoxy, $F_3CO$—, halogen, nitro, CN, —OH, —$CONHR^5$ and/or —$COOR^5$ ($R^5$ hydrogen, $C_1$–$C_4$-alkyl, phenyl or benzyl);

—O—$R^6$ where $R^6$ is hydrogen or an aliphatic radical which has up to 4 carbon atoms and can carry one of the following radicals: —$COOR^4$, —$CONHR^4$, —$NHCOR^4$, —$NHSO_2R^4$, —OH or phenyl, $R^2$ hydrogen, $C_1$–$C_4$-alkyl or phenyl, $R^3$ hydrogen or the radical —$(CH_2)_m$—$R^7$, where m is 0, 1, 2, 3 or 4, and $R^7$ is hydrogen, $C_1$–$C_4$-alkyl, phenyl, phenylsulfonyl, $NO_2$, CN, —COO—$(CH_2)_n$—$R^8$, —CONH—$(CH_2)_n$—$R^8$, —$CONHSO_2R^4$, —CO—$R^8$, —CH=CH—$CONHR^8$, —CH=CH—$COOR^8$, —CH=$NOR^8$, —$CH_2$—$NR^8R^9$, $CH_2NH$—CY—$(CH_2)_nR^9$, $CH_2NH$—CY—X—$(CH_2)_n$—$R^9$, $CH_2NH$—CO—$CF_3$, $CH_2NH$—$SO_2$—$R^9$

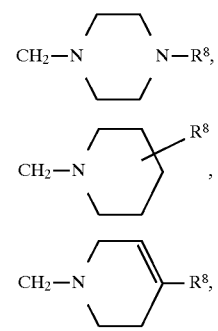

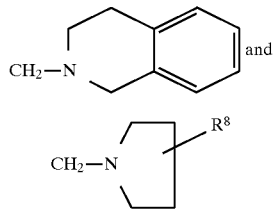

where x and Y are, independently of one another, oxygen or NH, n is 0, 1, 2, 3 or 4, $R^8$ is hydrogen or linear and branched $C_1$–$C_4$-alkyl which can be substituted by one or two phenyl or pyridyl radicals, and $R^9$ is hydrogen, linear or branched $C_1$–$C_6$-alkyl, phenyl or pyridyl, where all the phenyl or pyridyl radicals contained in $R^8$ and $R^9$ can carry one or two of the following radicals: O—$C_1$–$C_4$-alkyl, F, Cl, Br, I, $C_1$–$C_4$-alkyl, $NO_2$, $CF_3$, —$COOR^5$, —$CONHR^5$, $NH_2$, CN, —$SO_2Ph$, —$NHSO_2R^5$, —$NHCOR^5$, OH, —$SO_2$—$C_1$–$C_4$-alkyl, —$NHCOCF_3$, —$SO_2R^5$ and —$OCF_3$.

Preferred compounds of the formula I, their tautomeric and isomeric forms are those where the variables have the following meanings:

$R^1$ hydrogen; an aliphatic radical which has 1 or 2 [lacuna] and can carry one or two different substituents of the formula —$COOR^4$ where $R^4$ is hydrogen or $C_1$–$C_4$-alkyl,
—O—$R^6$ where $R^6$ is hydrogen or a $CH_2$ group which can carry one of the following radicals: —$COOR^4$ or phenyl, $R^2$ hydrogen $R^3$ hydrogen or the radical —$(CH_2)_m$—$R^7$ where m is 0 and $R^7$ is —COO—$(CH_2)_n$—$R^8$, —CONH—$(CH_2)_n$—$R^8$, —CO—$R^8$, —$CH_2$—$NR^8R^9$, $CH_2NH$—CY—$(CH_2)_n$—$R^9$, $CH_2NH$—CY—X—$(CH_2)_n$—$R^9$, $CH_2NH$—CO—$CF_3$, $CH_2NHSO_2R^9$ or

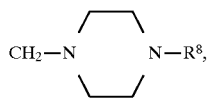

where X and Y are, independently of one another, oxygen or NH, n is 0, 1 or 2, $R^8$ is hydrogen or linear and branched $C_1$–$C_4$-alkyl which can be substituted by a phenyl radical, and $R^9$ is hydrogen, linear or branched $C_1$–$C_6$-alkyl or phenyl, where all the phenyl radicals contained in $R^8$ and $R^9$ can carry one or two of the following radicals: O—$C_1$–$C_4$-Alkyl, F, Cl, $C_1$–$C_4$-Alkyl, $NO_2$, $CF_3$, —$COOR^5$, —$CONHR^5$, $NH_2$, CN, —$SO_2Ph$, —$NHSO_2R^5$, —$NHCOR^5$, OH, —$SO_2$—$C_1$–$C_4$-Alkyl, —$NHCOCF_3$, —$SO_2R^5$ and —$OCF_3$ ($R^5$ hydrogen, $C_1$–$C_4$-alkyl, phenyl or benzyl).

The compounds I according to the invention can be prepared by various routes as shown in the following reaction schemes.

Scheme 1:

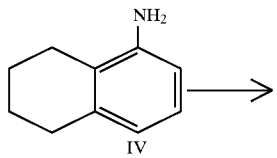

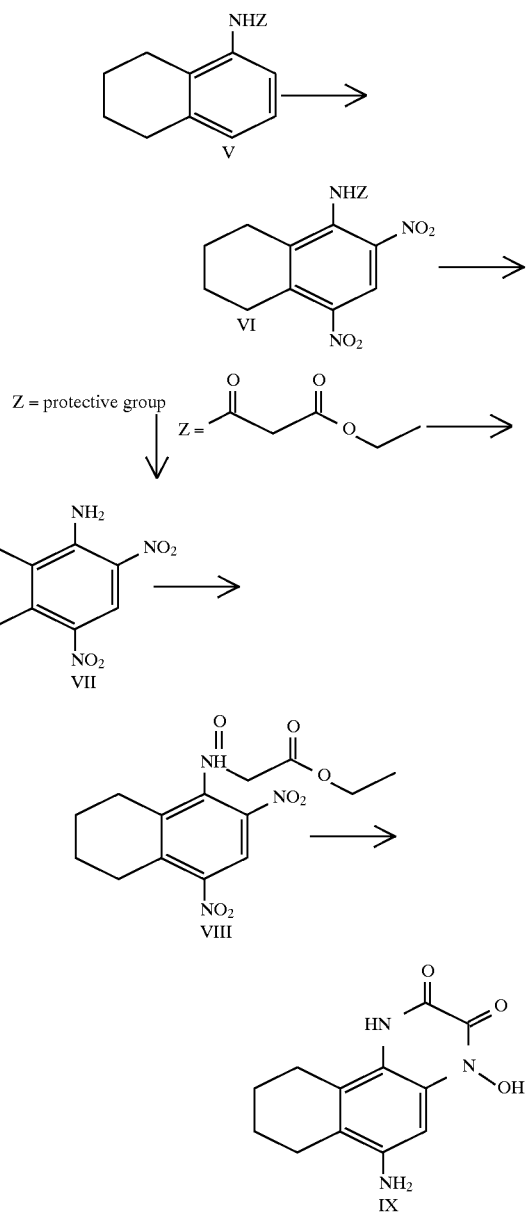

5-Aminotetralin (IV) is converted into the required derivative V where Z is a protective group such as acetyl and trifluoroacetyl. Further possible protective groups and possibilities for the introduction are listed in Th. W. Green and P. G. M. Wuts, "Protective Groups in Organic Synthesis", Wiley & Sons 1991, Chapter 7. V is nitrated in a similar manner to conventional processes listed in, for example, Houben-Weyl, "Methoden zur organischen Chemie", Vol. 10/1. This is carried out mainly with or without solvents such as sulfuric acid and acetic acid using nitrating agents such as potassium nitrate and nitric acid at 0°–50° C., preferably at 0°–25° C.

When Z is —CO—COOEt, VI can be reduced directly to the quinoxalinedione IX. This reduction is preferably carried out catalytically with hydrogen in polar solvents such as alcohols and dimethylformamide. Examples of catalysts which can be used are palladium/carbon or platinum/carbon.

In other cases, the protective group Z in VI is eliminated hydrolytically using acids, eg. hydrochloric acid, or bases, eg. sodium hydroxide solution, at 25°–100° C. The aniline obtained in this way is reacted with oxalic acid derivatives to give the oxanilide VIII. This amide formation is carried out by conventional processes listed, for example, in Houben-Weyl, "Methoden der organischen Chemie" Vol. E5, Chapter V. The reduction with subsequent ring closure of XIII to give the quinoxalinedione IX has been described above.

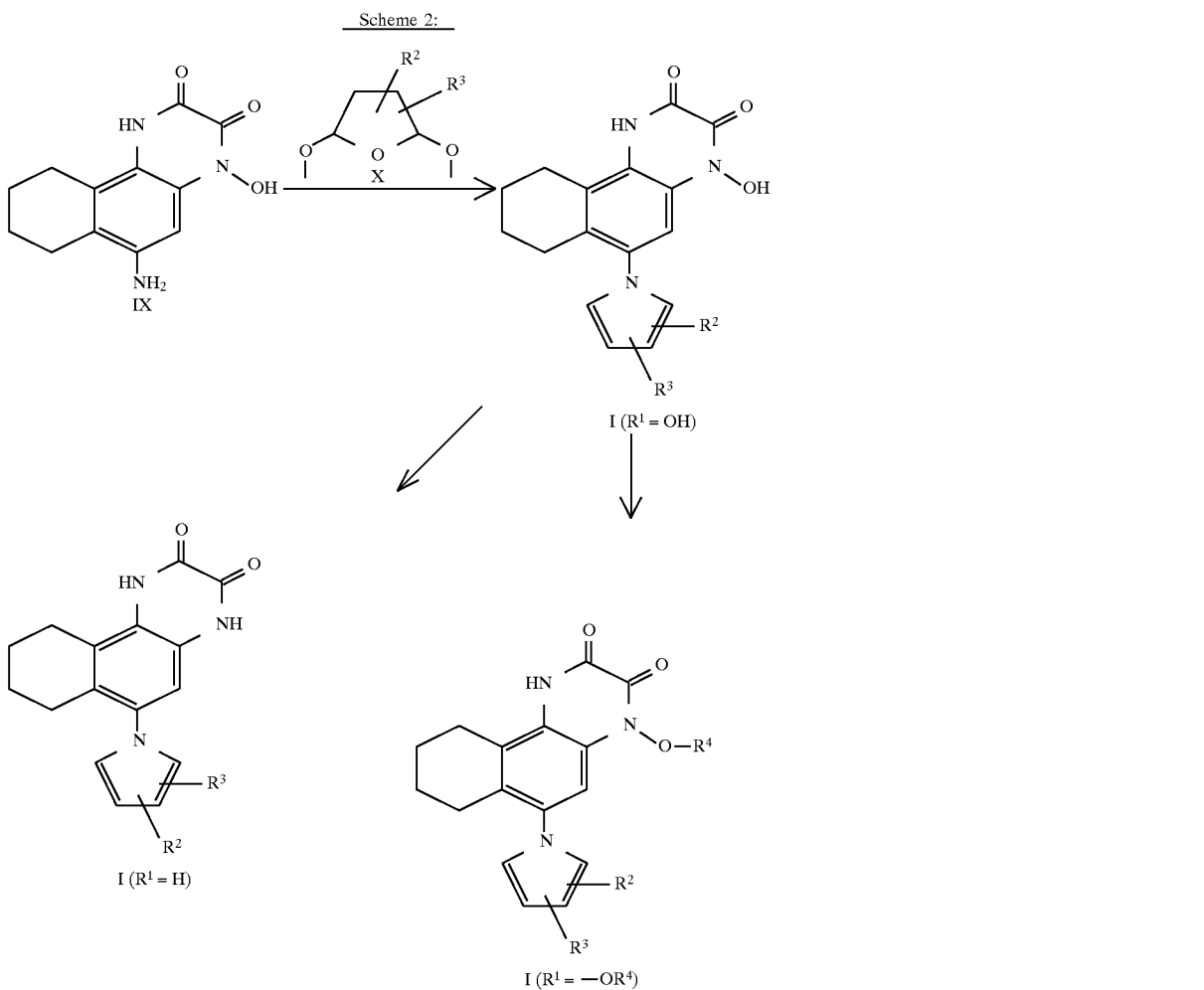

The aniline IX is reacted with a 1,4-dicarbonyl compound [sic] X such as succinaldehyde derivatives or cyclic or acyclic acetals derived therefrom to give pyrroles I ($R^1$=OH). This is carried out by conventional processes which are described, for example, by C. Ferri in Reaktionen der organischen Synthese, Thieme-Verlag 1978, pages 708 et seq., and which are discussed in more detail hereinafter.

The pyrrole derivative I ($R^1$=OH) can then be reduced to the analogous compounds I ($R^1$=H). This reduction is likewise carried out by conventional methods, but preferably with iron in acetic acid at 50°–120° C.

It is likewise possible to alkylate the pyrrole derivative I ($R^1$=OH) on the hydroxyl group to give I ($R^1$=—$OR^4$) using $R^4$-halogen. This reaction is carried out in polar solvents such as dimethylformamide, alcohols, water or mixtures thereof, and the bases used are, depending on the solvent, for example alcoholates, carbonates and hydrogen phosphates. The reaction is carried out at 0°–70° C., preferably at room temperature.

Scheme 3:
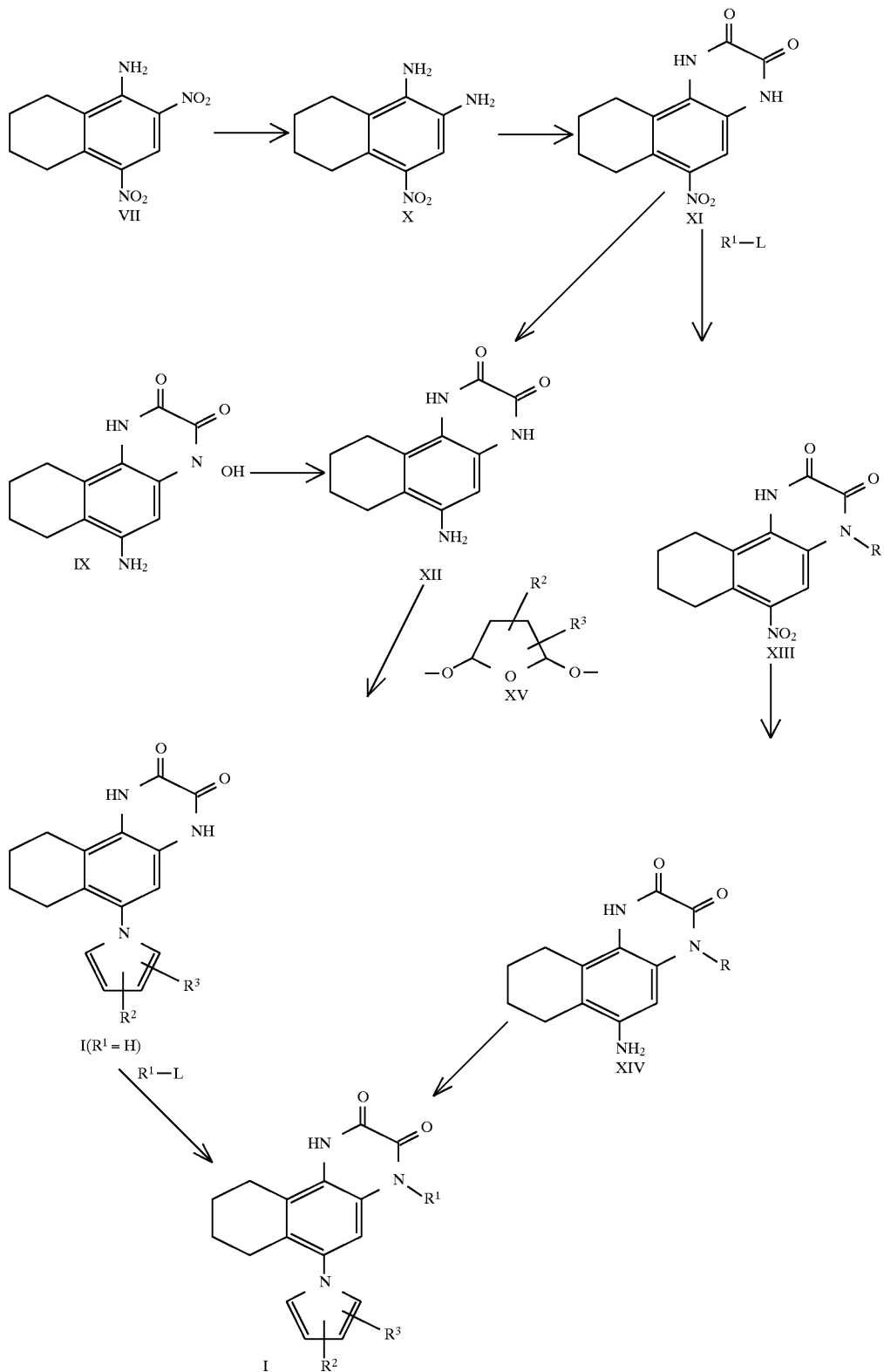

The compound VII (Scheme 1) can also be reduced to the orthodiamino derivative X. This reduction is mainly carried out with sulfur or sulfur compounds such as alkali metal sulfides, polysulf ides or analogous ammonium compounds. It is frequently carried out in aqueous media at alkaline pH values and elevated temperatures up to 100° C. These reduction methods are described in more detail in Houben-Weyl, "Methoden zur [sic] organischen Chemie", Vol. 11/1, Chapter IV.

The diamine X can subsequently be reacted with oxalic acid derivatives to give the quinoxalinedione XI. In the case of the oxalic diester, the compound X is heated with the diester without solvent, for example under ref lux, resulting in the product. If the oxalic acid monochloride is used, the procedure is as for amide syntheses (see R. C. Larock, Comprehensive Organic Chemistry, Chapter 9.4), and the resulting monoamide is subsequently heated with or without solvent, resulting in the product XI. If the diamide of X is obtained thereby, this is heated in aqueous acids such as hydrochloric acid with the addition of solubilizers such as tetrahydrofuran, resulting in the quinoxaline derivative XI. The nitro group in XI can subsequently be reduced, and the aniline XII is obtained.

This reduction can take place by chemical and by catalytic variants. In the catalytic method, for example, hydrogen on catalysts such as palladium/carbon and platinum/carbon is employed in solvents such as alcohols, tetrahydrofuran or dimethylformamide, it also being possible, however, to use chemical substances such as ammonium formate as hydrogen donors. Reduction by the chemical route takes place with metals or metal salts such as iron and tin in the presence of acids such as hydrochloric acid and acetic acid, usually at elevated temperature, eg. 60°–120° C. Further possibilities for the reduction are detailed in Houben-Weyl, Methoden der organischen Chemie, Vol. 11/1, Chapter IV.

The aniline XII can likewise be prepared from the N-hydroxyquinoxalinedione IX by chemical reduction (see above). XII is reacted by a Paal-Knorr method with 1,4-dicarbonyl compounds to give the pyrrole I (R$^1$=H). This takes place in a conventional way as described, for example, in C. Ferri,, "Reaktionen der organischen Synthese", Thieme-Verlag, 1978, pages 708 et seq. 1,4-Dicarbonyl compounds such as aldehydes, ketones, keto aldehydes or acetals thereof, which may, as in XV, also be cyclic, are used as reaction component. Catalytic amounts of acids such as acetic acid or toluenesulfonic acid are present, with elimination of water, in solvents. The acid can also act as solvent if used in large amounts. However, in general, the reaction is carried out in solvents such as toluene or in a mixture of solvents such as toluene/dimethylformamide with acid catalysis at 50°–150° C., preferably 100°–150° C., or in concentrated acetic acid at 50° C. up to the boiling point.

The quinoxaline I (R$^1$=H) in Scheme 3 can then be alkylated with a compound R$^1$—L to give I where L is a leaving group and can be, for example, halides (chlorine, bromine, iodine), triflates and tosylates. This alkylation is carried out in polar aprotic solvents such as tetrahydrofuran and dimethylformamide at from −10° to 100° C., with the quinoxalinedione I (R$^1$=H) initially being deprotonated with bases such as sodium hydride or potassium tertbutoxide and subsequently R$^1$—L being added.

It is also possible as an alternative to rearrange this sequence of stages, with XI initially being alkylated, and the XIII obtained in this way being converted via reduction to XIV into the pyrrole I (see Scheme 3).

Scheme 4:

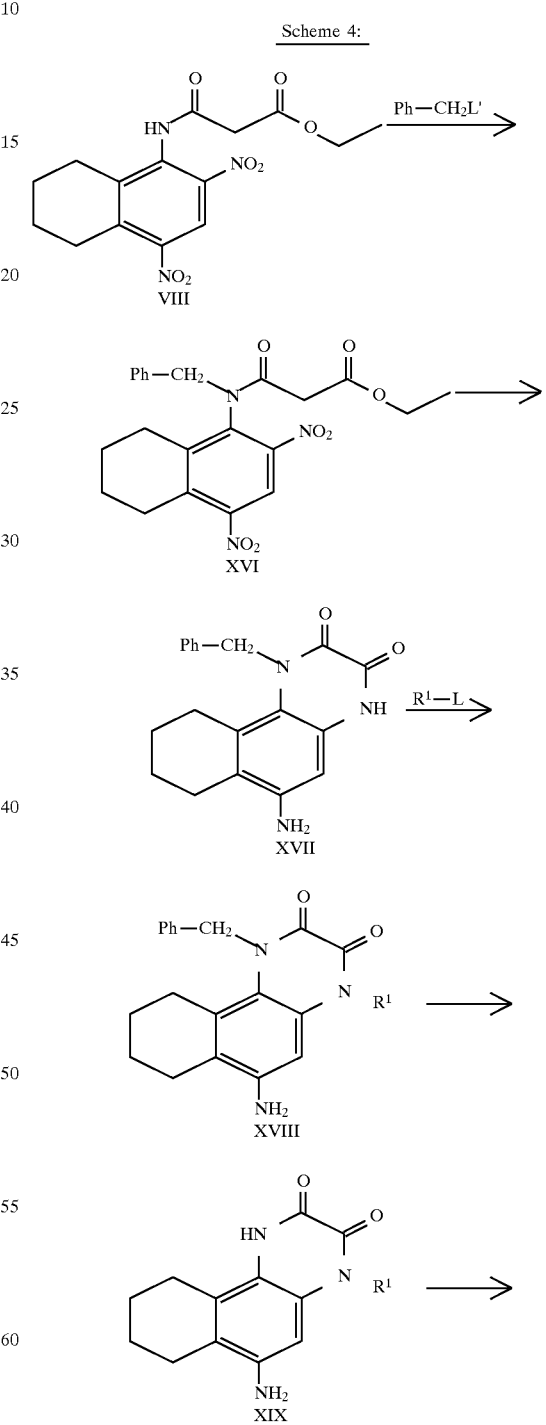

Scheme 4:

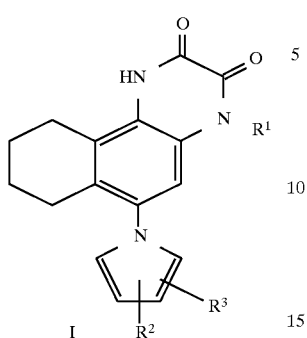

Another synthesis is depicted in Scheme 4. The oxalic amide VIII is alkylated to the derivative XVI. This is carried out in polar aprotic solvents such as tetrahydrofuran and dimethylformamide, with VIII initially being deprotonated with bases such as sodium hydride or potassium tert-butanolate and subsequently the alkylating reagent PhCH$_2$L' being added, where L' can be a leaving group like L (see Scheme 3). This reaction is carried out at 0°–100° C.

The dinitro compound XVI is subsequently reduced to the quinoxalinedione XVII. This reduction is carried out as in Scheme 1 and 2, preferably using in this case iron in glacial acetic acid at 100° C. to the boiling point. XVII is alkylated with R$^1$—L as in Scheme 3 (synthesis of I or XIII), where L is a leaving group such as halide.

The quinoxalinedione XVIII is then converted by catalytic hydrogenation into the derivative XIX. This catalytic hydrogenation is carried out as described previously in solvents such as tetrahydrofuran, alcohols and dimethylformamide using hydrogen or hydrogen donors such as ammonium formate in the presence of a catalyst such as palladium/carbon or platinum/carbon.

The aniline XIX subsequently reacts with a 1,4-dicarbonyl compound or a derivative thereof in a Paal-Knorr synthesis as in Scheme 3 to give the pyrrole I according to the invention.

The substitution of the claimed pyrrolyl ring in the products Ia prepared in this way can be modified in a suitable manner (Scheme 5). Thus, the aldehyde can be converted by reductive amination with amines into the compounds Ib according to the invention. The reductive amination is generally carried out at from 5° to 80° C., preferably 10° to 30° C., in the presence of reducing agents such as sodium cyanoborohydride or hydrogen in the presence of a hydrogenation catalyst such as Pd/carbon, Pt/carbon or Raney nickel, expediently in polar organic solvents such as alcohols or dimethylformamide.

Scheme 5:

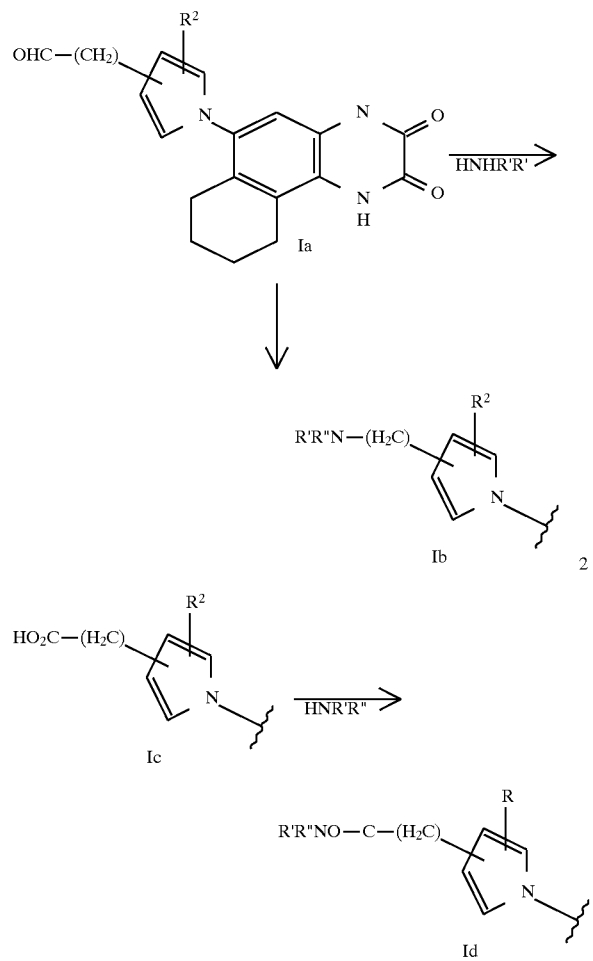

The aldehyde Ia can be oxidized by conventional processes, which [lacuna], for example, in R. C. Larock, "Comprehensive Organic Transformations", 1989, VCH Publisher, pages 838 et seq., to the carboxylic acid Ic according to the invention, in particular using potassium permanganate in solvents such as acetone at 25°–60° C. These carboxylic acids Ic are converted by reaction with amines NHR'R" into the amides Id. The coupling takes place by known processes which are listed, for example, in Houben-Weyl, "Methoden der organischen Chemie", Volume E5, Chapter V.

The pyrrolylalkylamines can likewise be reacted with isocyanates to give the ureas Ig, it also being possible to use, in place of the isocyanates, amines HNR'R" which are previously reacted in a known manner with phosgene or analogous compounds such as carbonyldiimidazole (=CDI). These and comparable processes are described, for example, in Houben-Weyl "Methoden der organischen Chemie", Volume E4, pages 334 et seq. These processes are carried out with or without solvent, preferably dimethylformamide, and at 25°–150° C.

Scheme 6:

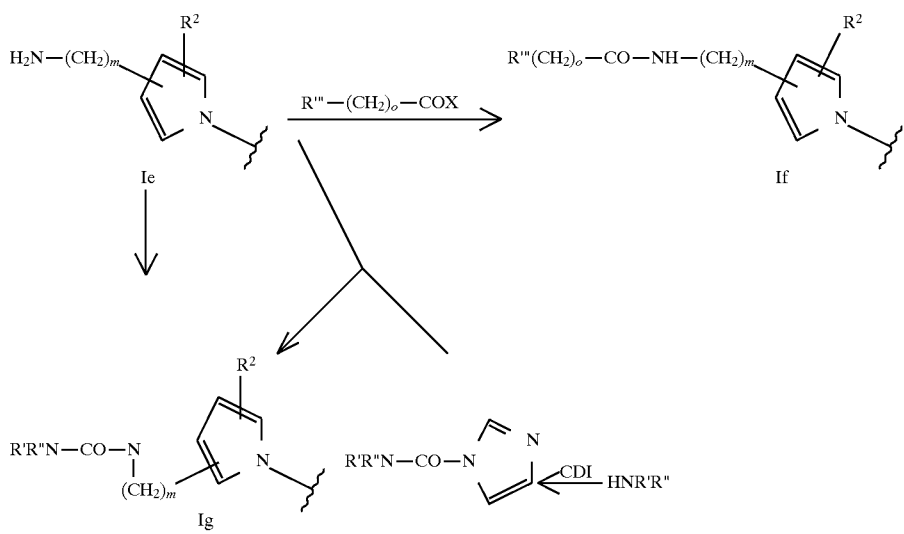

The pyrrolylalkylamines Ie obtainable as in Scheme 5 can be converted with acids R'"—$(CH_2)_oCO_2H$, which are activated in a suitable manner to R'"$(CH_2)_o$COL" where L" is a leaving group such as azide, imidazole and others which are listed in R. C. Larock, Comprehensive Organic Transformations, New York 1989, pages 972 et seq., into the amides If according to the invention. This coupling takes place by known processes which are listed, for example, in Houben-weyl "Methoden der organischen Chemie", Volume E5, Chapter V.

The compounds according to the invention are antagonists of the excitatory amino acid glutamate, especially antagonists of the glycine binding site of the NMDA receptor, of the AMPA receptor and of the kainate receptor.

The pharmacological activity of the compounds I was investigated on isolated membrane material from rat cerebra. For this purpose, the membrane material was treated in the presence of the compounds according to the invention with the radiolabelled substances $^3$H-2-amino-3-hydroxy-5-methyl-4-isoxazolepropionic acid ($^3$H-AMPA), [$^3$H]-glycine or [$^3$H]-kainates [sic], the latter binding to specific receptors (AMPA, NMDA or kainate receptors). The radioactivity of the treated membranes was then measured by scintillation counting. It was possible to determine from the bound radioactivity the amounts of bound $^3$H-AMPA, [$^3$H]-glycine or [$^3$H]-kainate, or in each case the displaced amounts of these radiolabelled substances. The dissociation constant $K_I$ (I=inhibitor) which emerges from this and is a measure of the displacing action of the agent according to the invention was found by iterative nonlinear regression analysis using the statistical analysis system (SAS) on an IBM computer, similar to the "Ligand" program of P. J. Munson and D. Rodbard (Analytical Biochem. 107, (1980) 220, ligand: Versatile Computerized Approach for Charakterization of Ligand Binding Systems).

The following in-vitro investigations were carried out:
1. Binding of $^3$H-2-amino-3-hydroxy-5-methyl-4-isoxazolepropionic acid ($^3$H-AMPA)

To prepare the membrane material, freshly removed rat cerebra were homogenized together with 15 times the volume of a buffer solution A composed of 30 mM α,α,α-tris (hydroxymethyl)methylamine hydrochloride (TRIS-HCl) and 0.5 MM ethylenediaminetetraacetic acid (EDTA), pH 7.4, using an UltraTurrax®. The suspension was centrifuged at 48,000× g for 20 min. After removal of the supernatant liquid, the protein-containing membrane material in the sediment was washed three times by suspension in buffer solution A and subsequent centrifugation at 48,000× g for 20 minutes each time. The membrane material was then suspended in 15 times the volume of buffer solution A and incubated at 37° C. for 30 min. The protein material was subsequently washed twice by centrifugation and suspension and stored at −70° C. until used.

For the binding assay, the protein material was thawed at 37° C. and washed twice by centrifugation at 48,000× g (20 min) and subsequent suspension in a buffer solution B composed of 50 mM TRIS-HCl, 0.1M potassium thiocyanate and 2.5 mM calcium chloride, pH 7.1. Subsequently, 0.25 mg of membrane material, 0.1 μCi of $^3$H-AMPA (60 Ci/mmol) and compound I and 1 ml of powder [sic] solution B were dissolved [sic] and incubated on ice for 60 min. The incubated solution was filtered through a CF/B filter (from Whatman) which had previously been treated with a 0.5% strength aqueous solution of polyethyleneimine for at least 2 h. The membrane residue was then washed with 5 ml of cold buffer solution B in order to separate bound and free $^3$H-AMPA from one another. After measurement of the radioactivity of the bound $^3$H-AMPA in the membrane material by scintillation counting, the $K_I$ was determined by regression analysis of the displacement plots.

A $K_I$ of <10 μm was found for 9-(1-pyrrolyl)-5,6,7,8-tetrahydrobenzo [f]quinoxaline-2,3-(1H,4H)-dione (Example 3). The substance is more active than the related substances of Example 20 in EP 573 221 and Example 16 in EP 283 959.

2. Binding of [$^3$H]-glycine

To prepare the membranes for the $^3$H-glycine binding assay, freshly removed rat hippocampi were homogenized in 10 times the volume of preparation buffer (50 mM Tris-HCl, 10 mM EDTA) using a Potter homogenizer. The homogenate was centrifuged at 48,000× g for 20 min. The supernatant was discarded, and the membranes present in the pellet were washed 2× by resuspension and centrifugation at 48,000× g (20 min each time). The resuspended membranes were frozen in liquid nitrogen and re-thawed at 37° C. After another washing step, the membrane suspension was incubated in a shaking water bath at 37° C. for 15 min. After a further 4 washing steps (centrifugation at 48,000× g for 20 minutes each time and resuspension in preparation buffer) the membranes were stored at −70° C. until used further.

The frozen membranes were thawed at 37° C. and washed 2× by centrifugation at 48,000× g (20 min) and subsequent resuspension in binding buffer (50 mM Tris-HCl pH 7.4, 10 mM MgCl$_2$). An incubation mixture contained 0.25 mg of protein (membranes), 25 nM $^3$H-glycine (16 Ci/mmol) and the substances to be tested in a total of 0.5 ml of binding buffer. The nonspecific binding was determined by adding 1 mM glycine. After incubation at 4° C. for 60 min, bound and free ligand were separated from one another by filtration through GF/B filters and subsequent washing with about 5 ml of ice-cold binding buffer. The radioactivity remaining on the filters is determined by liquid scintillation counting. The dissociation constants were calculated from the displacement plots using an iterative nonlinear fitting program or in accordance with the equation of Cheng and Prusoff.

3. Binding of [$^3$H]-kainate

To prepare the membranes for the [$^3$H]-kainate binding assay, freshly removed rat cerebra were homogenized in 15 times the volume of preparation buffer (30 mM Tris-HCl pH 7,4, 0,5 mM EDTA) using an Ultra-Turrax$_R$. The homogenate was centrifuged at 48,000× g for 20 min. The supernatant was discarded, and the membranes present in the pellet were washed a total of 3× by resuspension in preparation buffer and centrifugation at 48,000× g (20 min each time). After the third washing step, the membranes were washed 2× by centrifugation and resuspension and stored at −70° C. until used further.

The frozen membranes were thawed at 37° C., suspended in binding buffer (50 mM Tris-HCl pH 7.4) and centrifuged at 48,000× g for 20 min. The membranes present in the pellet were resuspended in binding buffer. An incubation mixture contained 0.25 mg of protein (membranes), 0.058 μCi (58 Ci/mmol) [lacuna] and the substances to be tested in a total of 1 ml of binding buffer. The nonspecific binding was determined in the presence of 0.1 mM glutamate. After incubation on ice for 60 minutes, bound and free ligand were separated from one another by filtration through CF/B filters and subsequent washing with 5 ml of ice-cold binding buffer. The CF/B filters had previously been treated with 0.5% polyethyleneimine for at least 2 h. The displacement plots were analyzed, and the dissociation constants were calculated using a nonlinear fitting program or in accordance with the equation of Cheng and Prusoff.

The compounds I according to the invention are suitable as drugs for human and veterinary medicine and can be used to produce drugs for the treatment of neurodegenerative disorders such as Parkinson's disease and Huntington's chorea, and neurotoxic disturbances of the central nervous system such as cerebral apoplectic insults (eg. stroke) and traumatic lesions of the brain and the spinal cord, and for producing antiepileptics, anxiolytics and antidepressants.

The drug preparations according to the invention contain a therapeutically effective amount of the compounds I in addition to conventional pharmaceutical auxiliaries. For local external use, eg. in dusting powders and ointments, the agents can be present in conventional concentrations. The agents are, as a rule, present in an amount of from 0.0001 to 1% by weight, preferably 0.001 to 0.1% by weight.

For internal use, the preparations are administered in single doses. From 0.1 to 100 mg per kg of body weight are administered in a single dose. The preparations can be administered in one or more doses each day, depending on the nature and severity of the disorders.

Appropriate for the required mode of administration, the drug preparations according to the invention contain conventional excipients and diluents in addition to the agent. Pharmaceutical auxiliaries possible for local external use are, for example, ethanol, isopropanol, ethoxylated castor oil, ethoxylated hydrogenated castor oil, polyacrylic acid, polyethylene glycol, polyethylene glycostearate [sic], ethoxylated fatty alcohols, liquid paraffin, petrolatum and lanolin. Examples suitable for internal use are lactose, propylene glycol, ethanol, starch, talc and polyvinylpyrrolidone.

It is furthermore possible for antioxidants such as tocopherol and butylated hydroxyanisole and butylated hydroxytoluene, flavor-improving additives, stabilizers, emulsifiers and lubricants to be present.

The substances present in the preparation in addition to the agent, and the substances used in the production of the pharmaceutical preparation, are toxicologically acceptable and compatible with the agent in each case. The drug preparations are produced in a conventional way, for example by mixing the agent with the other [sic] conventional excipients and diluents.

The drug preparations can be administered in various ways, such as orally, parenterally, subcutaneously, intraperitoneally and topically. Thus, possible presentations are tablets, emulsions, infusion and injection solutions, pastes, ointments, gels, creams, lotions, dusting powders and sprays.

EXAMPLES

Examples 1

9-(3-Formyl-1-pyrrolyl)-1-hydroxy-5,6,7,8-tetrahydrobenzo[f]quinoxaline-2,3 [1H,4H]dione

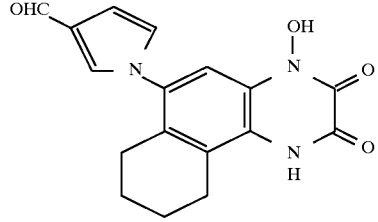

a) Ethyl 5,6,7,8-tetrahydro-1-naphthyloxamate 100 g (0.68 mol) of 5,6,7,8-tetrahydro-1-naphthylamine and 188 ml (1.36 mol) of triethylamine were dissolved in 1.5 l of anhydrous tetrahydrofuran and, at 0°–5° C., 102.5 g (0.75 mol) of ethyl oxalyl chloride were added dropwise. The mixture was then stirred for 30 min. The precipitate was filtered off with suction, and the filtrate was concentrated under reduced pressure. The residue was recrystallized from ethanol. 159 g (95%) of product were obtained.

$^1$H-NMR (D$_6$-DMSO): δ=1.3 (3H); 1.7 (4H); 2.6 (2H); 2.8 (2H); 4.3 (2H); 6.9–7.3 (3H) and 10.2 (1H) ppm.

b) Ethyl 2,4-dinitro-5,6,7,8-tetrahydro-1-naphthyloxamate 159 g (0.64 mol) of product 1a were dissolved in 1.5 l of concentrated sulfuric acid. At about 10° C., 83 ml of 98% strength nitric acid were slowly added dropwise, and the mixture was stirred for 30 min. It was then cautiously poured onto a large amount of ice, and the precipitate was filtered off with suction. 122 g (56%) of product were obtained.

$^1$H-NMR (D$_6$-DMSO): δ=1.3 (3H); 1.7 (4H); 2.8 (2H); 3.0 (2H); 4.3 (2H); 8.4 (1H) and 11 (1H) ppm.

c) 9-Amino-1-hydroxy-5,6,7,8-tetrahydrobenzo[f] quinoxaline-2,3-(1H,4H)-dione 120 g (0.36 mol) of product 1b were dissolved in 2 l of tetrahydrofuran and hydrogenated after addition of 5 g of Pd/carbon (10%). The mixture was then filtered, and the precipitate was thoroughly extracted by boiling with dimethylformamide. The combined organic phases were concentrated under reduced pressure, and the residue was treated with ethanol. The resulting precipitate was filtered off with suction. 57 g (65%) of product were obtained.

$^1$H-NMR (D6-DMSO): δ=1.7 (4H); 2.3 (2H); 2.7 (2H); ca. 5 (broad, NH$_2$); 6.8 (1H); 11.0 (1H) and 11.5 (broad) ppm.

d) 9-(3-Formyl-1-pyrrolyl)-1-hydroxy-5,6,7,8-tetrahydrobenzo-[f]quinoxaline-2,3(1H,4H)-dione 2.4 g (9.7 mmol) of product 1c and 1.5 g (9.7 mmol) of 2,5-dimethoxytetrahydrofuran-1-ylcarbaldehyde [sic] were refluxed in 100 ml of glacial acetic acid for 30 min. The mixture was then concentrated under reduced pressure. The residue was treated with ethanol and then with hot tetrahydrofuran and filtered off with suction. 2.3 g (74%) of product were obtained, melting point >250° C.

$^1$H-NMR (D$_6$-DMSO): δ=1.6 (2H); 1.8 (2H); 2.5 (2H); 2.8 (2H); 6.6 (1H); 7.0 (1H); 7.3 (1H); 7.8 (1H); 9.8 (1H) and ca. 11.3 (broad) ppm.

Example 2

9-(2,5-Dimethyl-1-pyrrolyl)-1-hydroxy-5,6,7,8-tetrahydrobenzo[f]quinoxaline-2,3(1H,4H)-dione

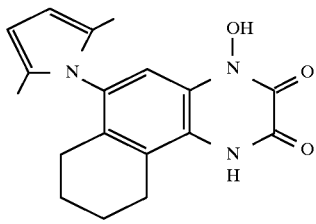

8 g (32.2 mmol) of product 1c and 3.8 ml (32.3 mmol) of hexane-2, 5-dione were reacted by method 1e [sic]. 7.2 g (69%) of product were obtained, melting point >250° C.

$^1$H-NMR (D$_6$-DMSO): δ=1.6 (2H); 1.8 (2H); 1.9 (6H); 2.1 (2H); 2.9 (1H); 5.8 (2H); 7.1 (1H); 11.4 (1H) and ca. 11.8 (broad) ppm.

Example 3

1-Hydroxy-9-(1-pyrrolyl)-5,6,7,8-tetrahydrobenzol[f]quinoxaline-2,3(1H,4H)-dione

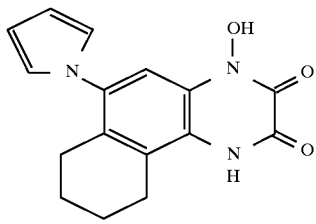

1.2 g (4.8 mmol) of product 1c and 0.61 g (4.8 mmol) of 2,5-dimethoxytetrahydrofuran were reacted by method 1e [sic]. 1.15 g (82%) of product were obtained, melting point >250° C.

$^1$H-NMR (D$_6$-DMSO): δ=1.6 (2H); 1.8 (1H); 2.5 (2H); 2.8 (1H); 6.2 (2H); 6.8 (2H); 7.2 (1H); 11.4 (1H) and ca. 12 (broad) ppm.

Example 4

1-Hydroxy-9-(3-trifluoromethylamidomethyl-1-pyrrolyl)-5,6,7,8-tetrahydrobenzo[f]quinoxaline-2,3 (1H,4H)-dione [sic]

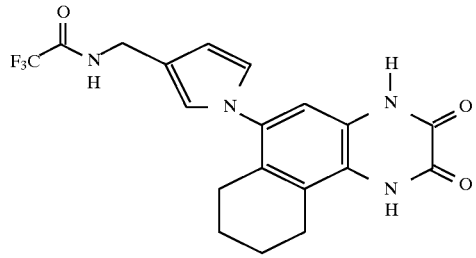

a) Preparation of N-((2,5-dimethoxy-3-tetrahydrofuranyl)methyl)-trifluoroacetamide 50 g (0.31 mol) of 3-aminomethyl-2,5-dimethoxytetrahydrofuran (DE 2 645 234), 31.7 g (0.31 mol) of triethylamine and a little 4-(N,N-dimethylamino) pyridine were dissolved in 300 ml of anhydrous ether and, at 0° to 5° C., 65.1 g (0.31 mol) of trifluoroacetic anhydride dissolved in 100 ml of anhydrous ether were added dropwise. The mixture was stirred for 1 h. It was then washed with water, dried and concentrated under reduced pressure. 70.5 g of impure product were obtained and were reacted further without purification.

b) 1-Hydroxy-9-(3-trifluoromethylamidomethyl-1-pyrrolyl)-5, 6,7,8-tetrahydrobenzo[f]quinoxaline-2,3(1H,4H)-dione 3 g (12.1 mmol) of product 1c and 3.1 g (12.1 mmol) of product 4a were reacted by method 1d. 3.9 g (77%) of product were obtained, melting point >230° C.

$^1$H-NMR (D$_6$-DMSO): δ=1.6 (2H); 1.8 (2H); 2.4 (2H); 2.8 (2H); 4.3 (2H); 6.2 (1H); 6.9 (2H); 7.2 (1H); 9.8 (1H); 11.4 (1H) and ca. 12 (broad) ppm.

Example 5

9-(3-Aminomethyl-1-pyrrolyl)-1-hydroxy-5,6,7,8-tetrahydrobenzo[f]quinoxaline-2, 3(1H,4H)-dione

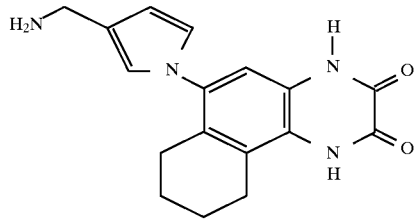

3.6 g (8.5 mmol) of Example 4 were dissolved in 30 ml of tetrahydrofuran, and 0.6 g (25.6 mmol) of lithiumhydroxide dissolved in 50 ml of water was added. The mixture was stirred at room temperature for about 2 h. The tetrahydrofuran was then removed under reduced pressure, and the resulting aqueous phase was made slightly acidic with dilute hydrochloric acid. After addition of aqueous sodium bicarbonate solution, the product precipitated (pH <7) and was filtered off with suction. 2.9 g (100%) were obtained, melting point >250° C.

$^1$H-NMR (CD$_3$COOD): δ=1.7 (2H).; 1.9 (2H); 2.5 (2H); 2.9 (2H); 4.2 (2H); 6.4 (1H); 6.8 (1H); 7.0 (1H) and 7.5 (1H) ppm.

Example 6

N-(1-(1-Hydroxy-5,6,7,8-tetrahydrobenzo[f]quinoxaline-2,3(1H,4H)-dion-9-yl)-3-pyrrolyl)methyl-N'-phenylurea [sic]

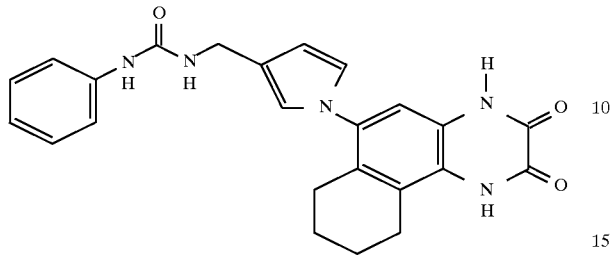

0.75 g (2.3 mmol) of the substance from Example 5 and 0.37 g (3.1 mmol) of phenyl isocyanate were heated in 30 ml of anhydrous dimethylformamide at 100° C. for 25 min. The mixture was then-concentrated under reduced pressure. The residue was dispersed in ethanol and filtered off with suction. 0.8 g (79%) of product was obtained, melting point >250° C.

$^1$H-NMR (D$_6$-DMSO): δ=1.7 (2H); 1.8 (2H); 2.5 (2H); 2.8 (2H); 4.2 (2H); 6.2 (1H); 6.3 (1H); 6.8–7.6 (8H); 8.4 (1H); 11.4 (1H) and ca. 12.0 (broad) ppm.

Example 7

9-(3-Benzoylaminomethyl-1-pyrrolyl)-1-hydroxy-5,6,7,8-tetrahydrobenzo[f]quinoxaline-2,3(1H,4H)-dione

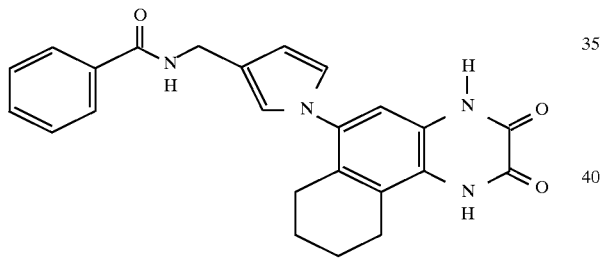

a) N-(2,5-Dimethoxy-3-tetrahydrofuranylmethyl)benzamide 2 g (12.4 mmol) of 2,5-dimethoxyl-3-aminomethyltetrahydrofuran and 3.4 ml (24.8 mmol) of triethylamine were dissolved in 50 ml of anhydrous tetrahydrofuran. At 0° C., 1.7 g (12.4 mmol) of benzoyl chloride dissolved in 20 ml of anhydrous tetrahydrofuran were added dropwise. The mixture was stirred for 1 h and then filtered, and the filtrate was concentrated under reduced pressure. The residue was reprecipitated from ether/petroleum ether. 2.4 g of product were obtained and were used without further purification.

b) 9-(3-Benzoylaminomethyl-1-pyrrolyl)-1-hydroxy-5,6,7,8-tetrahydrobenzo[f]quinoxaline 1.2 [lacuna] (4.8 mmol) of the substance from Example 5 and 1.3 g (4.8 mmol) of product 7a were refluxed in 70 ml of glacial acetic acid for 10 min. The mixture was then poured into ice-water, and the resulting precipitate was filtered off with suction. 1.6 g (77%) of product were obtained, melting point 212° C. (decomposition).

$^1$H-NMR (D$_6$-DMSO): δ=1.6 (2H); 1.8 (2H); 2.5 (2H); 2.8 (2H); 4.4 (2H); 6.2 (1H); 6.8 (2H); 7.2 (1H); 7.4–7.6 (3H); 7.9 (2H); 8.8 (1H); 11.4 (1H) and ca. 12 (broad) ppm.

Example 8

1-Benzyloxy-9-(2,5-dimethyl-1-pyrrolyl)-5,6,7,8-tetrahydrobenzo[f]quinoxaline-2,3(1H,4H)-dione

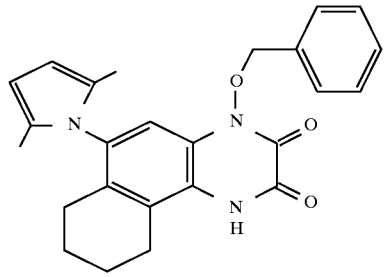

2.0 g (6.2 mmol) of the substance from Example 2 and 1.1 ml (9.4 mmol) of benzyl bromide were dissolved in 150 ml of ethanol, 50 ml of a phosphate buffer (1.22 g of potassium dihydrogen phosphate, 5.7 g of disodium hydrogen phosphate in 100 ml of water) were added, and the mixture was stirred at room temperature for 2 h. The ethanol was then removed under reduced pressure, and the resulting aqueous phase was acidified with 1M hydrochloric acid and extracted with ethyl acetate. The organic phase was dried and concentrated under reduced pressure, and the residue was treated with a little ethanol. 2.1 g (83%) of product were obtained, melting point 220° C. (decomposition).

$^1$H-NMR (D$_6$-DMSO): δ=1.6 (2H); 1.7–1.9 (8H); 2.0 (2H); 2.8 (2H) 5.2 (2H); 5.8 (2H); 7.0 (1H); 7.4–7.6 (5H) and ca. 11.5 (broad) ppm.

Example 9

9-(2,5-Dimethyl-1-pyrrolyl)-1-ethoxycarbonylmethoxy-5,6,7,8-tetrahydrobenzo[f]quinoxaline-2,3(1H,4H)-dione

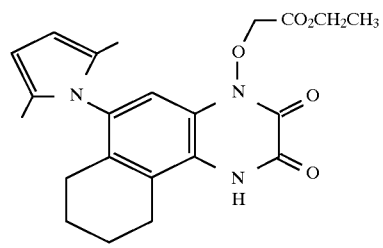

3.5 g (10.8 mmol) of the substance from Example 2 and 1.8 ml (16.4 mmol) of ethyl bromoacetate were reacted as in Example 8. 3.2 g (73%) of product were obtained, melting point 157°–158° C.

$^1$H-NMR (D$_6$-DMSO): δ=1.2 (3H); 1.6 (2H); 1.9 (2H); 1.95 (6H); 2.1 (2H); 2.9 (2H); 4.2 (2H); 5.0 (2H); 5.9 (2H); 7.4 (2H) and ca. 11.5 (1H) ppm.

Example 10

1-Carboxymethyloxy-9-(2,5-dimethyl-1-pyrrolyl)-5,6,7,8-tetrahydrobenzo[f]quinoxaline-2,3(1H,4H)-dione

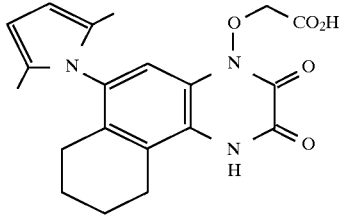

1.5 g (3.7 mmol) of the substance from Example 9 were dissolved in 70 ml of tetrahydrofuran and, at room temperature, 0.26 g (10.9 mmol) of lithium hydroxide dissolved in 10 ml of water was added. The mixture was stirred for 2 h. The tetrahydrofuran was then removed under reduced pressure, the resulting aqueous phase was acidified with 1M hydrochloric acid, and the resulting precipitate was filtered off with suction. 1.1 g (79%) of product were obtained, melting point >260° C.

$^1$H-NMR (D$_6$-DMSO): δ=1.6 (2H); 1.7–1.9 (8H); 2.1 (2H); 2.8 (2H); 4.8 (2H); 5.8 (2H); 7.4 (1H) and ca. 11.5 (1H) ppm.

Example 11

9-(3-Formyl-1-pyrrolyl)-5,6,7,8-tetrahydrobenzo[f]quinoxaline-2,3(1H,4H)-dione

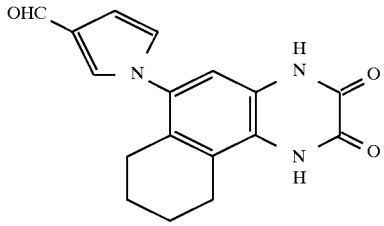

0.5 g (1.5 mmol) of the substance from Example 1 was refluxed in 25 ml of glacial acetic acid. Then 0.09 g (1.6 mmol) of iron powder was added in portions, and the mixture was heated for a further 10 min. It was then poured into water, and the precipitate was filtered off with suction. 0.44 g (94%) of product was obtained, melting point >250° C.

$^1$H-NMR (D$_6$-DMSO): δ=1.6 (2H); 1.8 (2H); 2.4 (2H); 2.8 (2H); 66 (1H); 6.9 (); 7.0 (1H); 7.8 (1H); 9.8 (1H); 11.2 (1H) and 12 (1H) ppm.

Example 12

9-(2,5-Dimethyl-1-pyrrolyl)-5,6,7,8-tetrahydrobenzo[f]quinoxaline-2,3(1H,4H)-dione

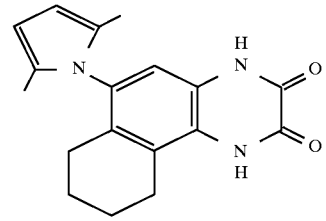

a) 9-Amino-5,6,7,8-tetrahydrobenzo[f]quinoxaline-2,3(1H,4H)-dione 20 g (0.08 mol) of product 1c were refluxed in 500 ml of glacial acetic acid, and 14 g (0.25 mol) of iron powder were added in portions. The mixture was then refluxed for a further hour. It was then filtered hot, and the filtrate was concentrated under reduced pressure. The resulting residue was treated with hot water, and the product was filtered off with suction. 17 g (61%) were obtained.

$^1$H-NMR (CD$_3$COOD): δ=1.8 (2H); 1.9 (2H); 2.5 (2H), 2.7 (2H) and 6.6 (1H) ppm.

b) 9-(2,5-Dimethyl-1-pyrrolyl)-5,6,7,8-tetrahydrobenzo[f]quinoxaline-2,3(1H,4H)-dione 3 g (11.5 mmol) of product 12a and 1.3 g (11.5 mmol) of hexane-2,5-dione were refluxed in 150 ml [lacuna] for 30 min. The mixture was then concentrated under reduced pressure, and the resulting residue was treated with water and filtered off with suction. The crude product was extracted by boiling with a little ethyl acetate. 1.8 g (49%) of product were obtained, melting point >265° C.

$^1$H-NMR (D$_6$-DMSO): δ=1.6 (2H), 1.7–1.9 (8H); 2.0 (2H); 2.8 (2H); 5.8 (2H); 6.8 (1H); 11.2 (1H) and 12 (1H) ppm.

Example 13

9-(1-Pyrrolyl)-5,6,7,8-tetrahydrobenzo[f]quinoxaline-2,3(1H,4H)-dione

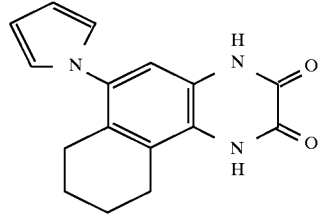

1 g (3.8 mmol) of product 12a and 0.5 g (3.8 mmol) of 2,5-dimethoxytetrahydrofuran were reacted by method 1d. 0.8 g (67%) of the product was obtained. Melting point >250° C.

$^1$H-NMR (D$_6$-DMSO): δ=1.6 (2H); 1.8 (2H); 2.4 (2H); 2.7 (2H); 6.2 (2H); 6.9 (3H); 11.2 (1H) and 12 (1H) ppm.

Example 14

9-(3-(4-Benzyl-1-piperazinyl)methyl-1-pyrrolyl)-5,6,7,8-tetraydrobenzo[f]quinoxaline-2,3(1H,4H)-dione difumarate

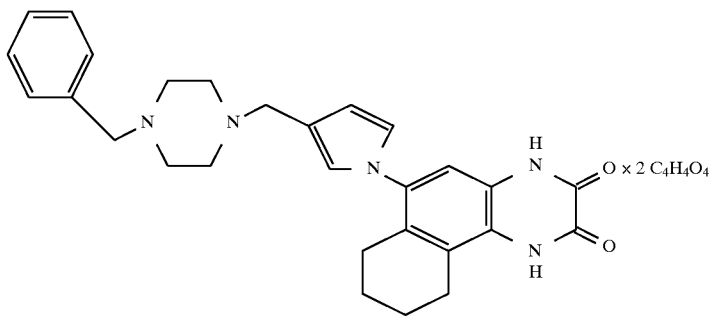

1.3 g (4.2 mmol) of the substance from Example 11, 1.5 g (8.4 mmol) of 4-benzylpiperazine and 0.25 g (4.2 mmol) of acetic acid were dissolved in 100 ml of dimethylformamide and, at room temperature, 0.26 g (4.2 mmol) of sodium cyanoborohydride was added in portions. The mixture was stirred for 16 h. It was subsequently concentrated under reduced pressure, and the residue was suspended in aqueous sodium bicarbonate solution. The precipitate was filtered off with suction and dissolved in tetrahydrofuran, twice the equimolar amount of fumaric acid in ethanol was added, and the mixture was boiled. After cooling, the product was filtered off with suction. 1.2 g (50%) of product were obtained, melting point >250° C.

$^1$H-NMR (D$_6$-DMSO): δ=1.6 (2H); 1.8 (2H); 2.3–2.8 (12H); 3.5 (2H); 3.6 (2H); 6.2 (1H); 6.4 (4H); 6.8 (2H); 6.9 (1H); 7.2–7.4 (5H); 11.1 (1H) and 11.9 (1H) ppm.

Example 15

9-(3-Trifluoromethylamidomethyl-1-pyrrolyl)-5,6,7,8-tetrahydrobenzo[f]quinoxaline-2,3(1H,4H)-dione

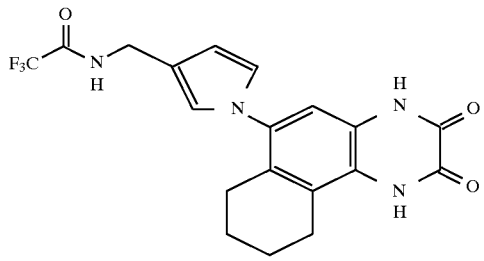

1.1 g (4.8 mmol) of substance [sic] of product 12a and 1.2 g (4.8 mmol) of product 4a were reacted by method 1e 1.4 g (76%) of the product were obtained. Melting point >240° C.

$^1$H-NMR (D$_6$-DMSO): δ=1.6 (2H; 1.8 (2H); 2.4 (2H); 2.8 (2H); 4.2 (2H); 6.2 (1H); 6.7 (2H); 6.8 (1H); 9.8 (1H); 11.2 (1H) and 12.0 (1H) ppm.

Example 16

9-(3-Aminomethyl-1-pyrrolyl)-5,6,7,8-tetrahydrobenzo[f]quinxaline-2,3(1H,4H)-dione

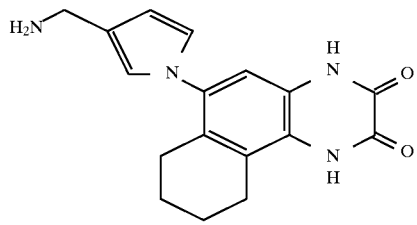

1.3 g (3.3 mmol) of product 15 were dissolved in 50 ml of tetrahydrofuran, and 0.32 g (13.3 mmol) of lithium hydroxide dissolved in 50 ml of water was added. The mixture was stirred at room temperature for 1 h. The tetrahydrofuran was then removed under reduced pressure, and the resulting aqueous phase was neutralized with 1M hydrochloric acid. The resulting precipitate was filtered off with suction. 1.1 g (100%) of product were obtained, melting point >220° C.

$^1$H-NMR (CD$_3$COOD): δ=1.75 (2H); 1.9 (2H); 2.6 (2H); 2.9 (2H); 4.2 (2H); 6.4 (1H); 6.8 (1H); 7.0 (1H) and 7.1 (1H) ppm.

Example 17

N-(1-(5,6,7,8-Tetrahydrobenzo[f]quinoxaline-2,3(1H,4H)-dion-9-yl)-3-pyrrolyl)methyl-N'-phenylurea

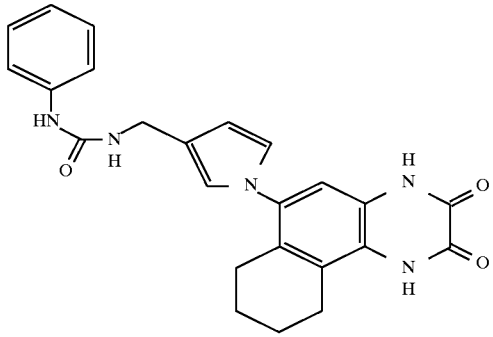

1.0 g (3.4 mmol) of the substance from Example 16 and 0.44 g (3.7 mmol) of phenyl isocyanate were heated in 30 ml of anhydrous dimethylformamide at 110° C. for 15 min. After cooling, the resulting precipitate was filtered off with suction and washed with ethanol. 1.12 g (66%) of product were obtained, melting point >240° C.

¹H-NMR (D₆-DMSO): δ=1.6 (2H); 1.8 (2H); 2.4 (2H); 2.8 (2H); 4.2 (2H); 6.2 (1H); 6.3 (1H); 6.8 (1H); 6.9 (3H); 7.2 (2H); 7.4 (2H); 8.4 (1H); 11.2 (broad) and 11.9 (broad) ppm.

Example 18

9-(3-(4-(1,1-Diphenylmethyl)-1-piperazinyl)methyl-1-pyrrolyl)-1-hydroxy-5,6,7,8-tetrahydrobenzo[f]quinoxaline-2,3(1H,4H)-dione

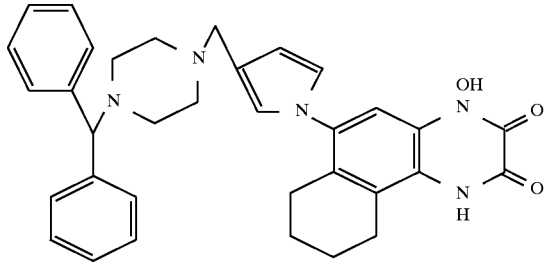

1.6 g (4.9 mmol) of Example 1 and 2.5 g (9.8 mmol) of 4-(1,1-diphenylmethyl)piperazine were reacted as in Example 14. 2.4 g (84%) of product were obtained, melting point >200° C.

¹H-NMR (CD₃COOD): δ=1.7 (2H); 1.9 (2H); 2.5 (2H); 2.9 (2H); 3.0–3.7 (8H); 4.3 (2H); 4.8 (1H); 6.4 (1H); 6.9 (1H); 7.1 (1H) and 7.2–7.6 (11H) ppm.

Example 19

9-(3-(4-Benzyl-1-piperazinyl)methyl-1-pyrrolyl)-1-hydroxy-5,6,7,8-tetrahydrobenzo[f]quinoxaline-2,3(1H,4H)-dione

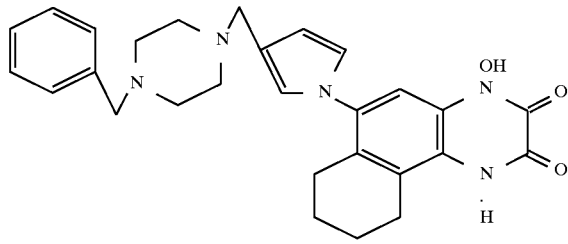

1.5 g (4.6 mmol) of 1 and 1.6 g (9.2 mmol) of 4-benzylpiperazine were reacted by method 14. 1.1 g (50%) of product were obtained, melting point >200° C.

¹H-NMR (CD₃COOD): δ=1.7 (2H); 1.9 (2H); 2.5 (2H); 2.9 (2H); 3.6–3.8 (8H); 4.3 (2H); 4.4 (2H); 6.4 (1H); 6.9 (1H); 7.05 (1H) and 7.4–7.6 (6H) ppm.

Example 20

1-Ethoxycarbonylmethyl-9-(3-formyl-1-pyrrolyl)-5,6,7,8-tetrahydrobenzo[f]quinoxaline-2,3(1H,4H)-dione

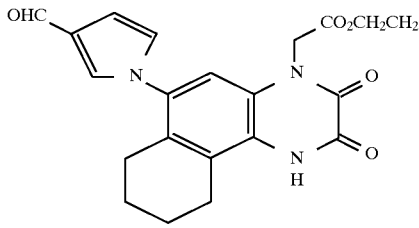

7 g (22.6 mmol) of the substance from Example 11 were dissolved under nitrogen in 100 ml of anhydrous dimethylformamide and, at room temperature, 0.7 g (22.6 mmol) of sodium hydride (80%) was added in portions. After 1 h, 2.8 ml (24.9 mmol) of ethyl bromoacetate were added dropwise, and the mixture was stirred for 16 h. It was then poured into water and extracted with ethyl acetate. The organic phase was dried and concentrated under reduced pressure. The residue was purified by chromatography on silica gel. 4.5 g (51%) of product were obtained, melting point >250° C.

¹H-NMR (D₆-DMSO): δ=1.2 (3H); 1.6 (2H); 1.8 (2H); 2.4 (2H); 2.8 (2H); 4.1 (2H); 5.0 (2H); 6.6 (1H); 7.0 (1H); 7.3 (1H); 7.8 (1 9.8 (1H) and 11.4 (1H) ppm.

Example 21

9-(3-(4-(1,1-Diphenylmethyl)-1-piperazinyl)methyl-1-pyrrolyl) 1-ethoxycarbonylmethyl-5,6,7,8-tetrahydrobenzo[f]quinoxaline-2,3(1H,4H)-dione

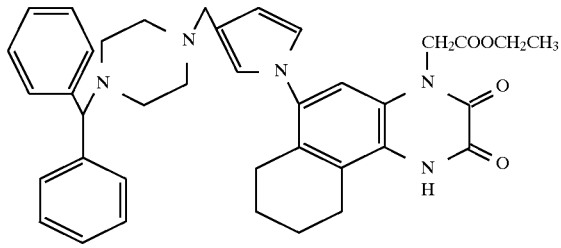

1.0 g (2.5 mmol) of the substance from Example 20 and 1.3 g (5.1 mmol) of 4-(1,1-diphenylmethyl)piperazine were reacted as in Example 14. 0.9 g (57%) of product was obtained, melting point >200° C.

¹H-NMR (D₆-DMSO): δ=1.2 (3H); 1.6 (2H); 1.8 (2H); 2.4 (2H); 2.8 (2H); 2.9–3.6 (10H); 4.2 (3H); 5.0 (2H); 6.4 (1H); 6.9 (1H); 7.0 (1H); 7.2 (1H); 7.2–7.6 (10H) and 11.3 (1H) ppm.

Example 22

9-(3-(4-Benzyl-1-piperazinyl)methyl-1-pyrrolyl)-1-ethoxycarbonylmethyl-5, 6,7, 8-tetrahydrobenzo[f]quinoxaline-2,3(1H, 4H)-dione

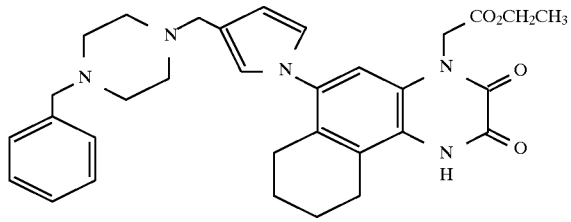

1 g (2.5 mmol) of the substance from Example 21 and 0.9 g (5.1 mmol) of 4-benzylpiperazine were reacted as in Example 14. 0.8 [lacuna] (58%) of product was obtained, melting point >220° C.

$^1$H-NMR (D$_6$-DMSO): δ=1.2 (3H); 1.6 (2H); 1.8 (2H); 2.4–2.7 (6H); 2.8 (2H); 3.2–3.6 (8H); 4.2 (2H); 5.0 (2H); 6.2 (1H); 6.6 (2H, fumarate); 6.8 (2H); 7.1 (1H); 7.2–7.4 (5H) and ca. 11.3 (1H) ppm.

Example 23

1-Carboxymethyl-9-(3-formyl-1-pyrrolyl)-5,6,7,8-tetrahydrobenzo[f]quinoxaline-2,3(1H,4H)-dione

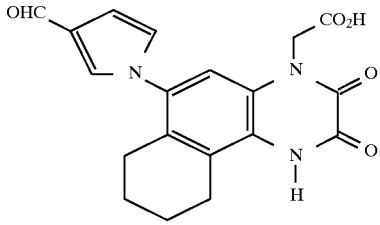

1 g (2.5 mmol) of the substance from Example 20 were added to 3 ml of tetrahydrofuran, and 10 ml (5 mmol) of a 0.5 molar solution of lithium hydroxide were added. The mixture was stirred at room temperature for 1 h. The tetrahydrofuran was then removed under reduced pressure, and the resulting aqueous phase was neutralized with dilute hydrochloric acid. The precipitate was filtered off with suction. 0.7 g (76%) of product was obtained, melting point >250° C. $^1$H-NMR (D$_6$-DMSO): δ=1.6 (2H); 1.8 (2H); 2.4 (2H); 2.8 (2H); 4.8 (2H); 6.6 (1H); 7.0 (1H); 7.2 (1H 9 [sic]; 7.7 (1H), 9.7 (1H) and ca. 11.3 (broad) ppm.

Example 24

1-Carboxymethyl-9-(3-(4-(1,1-diphenylmethyl)-1-piperazinyl)methyl-1-pyrrolyl)-5, 6,7,8-tetrahydrobenzo[f]quinoxaline-2,3(1H,4H)-dione

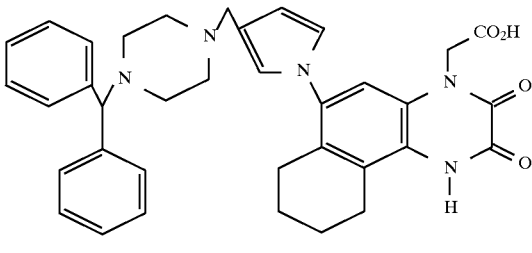

0.8 g (1.3 mmol) of the substance from Example 21 were hydrolyzed as in Example 23. 0.76 g (85%) of product was obtained, melting point >220° C.

$^1$H-NMR (CD$_3$COOD): δ=1.7 (2H); 1.9 (2H); 2.5 (2H); 2.9 (2H); 3.6 (4H); ca. 3.8 (broad, 4H); 4.3 (2H); 5.1 (2H); 5.4 (1H); 6.4 (1H); 6.8 (1H); 7.1 (1H); 7.3 (1H); 7.3–7.5 (6H) and 7.8 (4H)

Example 25

9-(2-Acetamidomethyl-1-pyrrolyl)-1-ethoxycarbonylmethyl-5,6,7,8-tetrahydrobenzo[f]quinoxaline-2,3(1H,4H)-dione

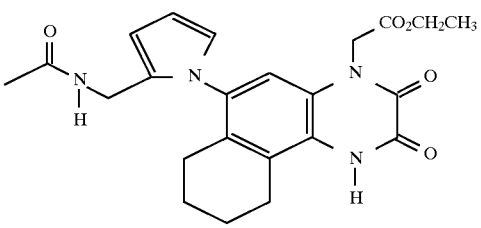

a) Ethyl N-benzyl-N-(2,4-dinitro-5,6,7,8-tetrahydro-1-naphthyl)oxamate 109.5 g (0.32 mol) of product 1b were dissolved in 1.25 l of anhydrous tetrahydrofuran and, at room temperature, 10.7 g (0.36 mol) of 80% sodium hydride were added in portions. A solution of 55.4 g=38.4 ml (0.32 mol) of benzyl bromide in 100 ml of anhydrous tetrahydrofuran was then added dropwise. After a further 50 ml of anhydrous dimethylformamide had been added, the mixture was refluxed for 7 h. It was subsequently concentrated under reduced pressure, the residue was partitioned between water and ethyl acetate, and the organic phase was dried and concentrated under reduced pressure. This residue was purified by chromatography on silica gel (mobile phase: cyclohexane/ethyl acetate =1/1). 108.4 g (78%) of product were obtained.

$^1$H-NMR (D$_6$-DMSO): δ=1.0 (3H); 1.4–1.9 (4H); 2.5–3.0 (4H); 4.0 (2H); 4.6 (1H); 5.1 (1H); 7.0–7.4 (5H) and 8.4 (1H) ppm.

b) 9-Amino-4-benzyl-5,6,7,8-tetrahydrobenzo[f]quinoxaline-2,3(1H,4H)-dione 107 g (0.25 mol) of product 25a were refluxed in 1.5 l of glacial acetic acid. Then 77 g (1.4 mol) of iron powder were added in portions, and the mixture was refluxed for 30 min. It was then poured into a large amount of water, and the resulting precipitate was filtered off with suction. 42.4 g (53%) of product were obtained, melting point 290° C.

$^1$H-NMR (D$_6$-DMSO): δ=1.4 (2H); 1.6 (2H); 2.4 (2H); 2.6 (2H); 4.9 (2H); 5.2 (2H); 6.4 (1H); 76.0–7.4 (5H) and 11.6 (1H) ppm.

c) 9-Amino-4-benzyl-1-ethoxycarbonylmethyl-5,6,7,8-tetrahydro-benzo[f]quinoxaline-2,3(1H,4H)-dione 41.5 g (0.13 mol) of product 25b were dissolved in 700 ml of anhydrous dimethylformamide and, at room temperature, 4.3 g (0.14 mol) of 80% sodium hydride were added in portions. A solution of 21.7 g (0.13 mol) of ethyl bromoacetate dissolved in 100 ml of anhydrous dimethylformamide was then added dropwise. The mixture was stirred at room temperature for 1 h and then poured into water and made weakly alkaline with sodium bicarbonate. The product was precipitated by adding sodium chloride and was filtered off with suction and thoroughly washed with ether. 45.4 g (86%) were obtained, melting point 231° C.

$^1$H-NMR (D$_6$-DMSO): δ=1.3 (3H); 1.5 (2H), 1.8 (2H), 2.4 (2H); 2.8 (2H); 4.2 (2H); 4.8 (1H); 5.0 (1H); 5.3 (2H); 6.4 (1H) and 7.0–7.4 (5H) ppm.

d) 9-Amino-1-ethoxycarbonylmethyl-5,6,7,8-tetrahydrobenzo[f]quinoxaline-2,3(1H,4H)-dione 44.5 g (0.11 mol) of product 25c were dissolved in 1,000 ml of dimethylformamide and hydrogenated after addition of 50 ml of acetic acid and 5 g of palladium/carbon (10%). The mixture was then filtered, and the filtrate was concentrated under reduced pressure. The residue was recrystallized from ethanol/ether. 30.4 g (88%) of product were obtained, melting point 238° C.

$^1$H-NMR (D$_6$-DMSO): δ=1.3 (3H); 1.8 (4H); 2.4 (2H); 2.7 (2H); 4.2 (2H); 4.9 (2H); 4.9 (2H), 6.3 (1H) and ca. 11 (1H) ppm.

e) N-[(2,5-Dimethoxy-2-tetrahydrofuranyl)methyl]acetamide 11.5[lacuna] (71.3 mmol) of 2-aminomethyl-2,5-dimethoxytetrahydrofuran and 20 ml (143 mmol) of triethylamine were dissolved in 150 ml of anhydrous tetrahydrofuran. At 0° C., a solution of 5 ml (71.3 mmol) of acetyl chloride in 50 ml of tetrahydrofuran was added dropwise, and the mixture was stirred for 1 h. The precipitate was filtered off and the filtrate was concentrated under reduced pressure. 12 g of crude product were obtained and were reacted further without purification.

f) 9-(2-Acetamidomethyl-1-pyrrolyl)-1-ethoxycarbonylmethyl5,6,7,8-tetrahydrobenzo[f]quinoxaline-2,3(1H,4H)-dione 3.2 g (10 mmol) of product 25e and 2.5 g (812.5 mmol) of product 25f [sic] were refluxed in 50 ml of glacial acetic acid for 20 min. The mixture was then poured into ice-water. The precipitate was filtered off with suction and the filtrate was extracted with ethyl acetate. The organic phase was dried and concentrated under reduced pressure. The residue was combined with the above precipitate. 1.9 g (43%) of product were obtained, melting point 269° C.

$^1$H-NMR (D$_6$-DMSO): δ=1.2 (3H); 1.5–1.9 (7H); 2.0–2.4 (2H); 2.8 (2H); 3.8 (1H); 4.0 (1H); 4.2 (2H); 5.0 (2H); 6.2 (2H); 6.7 (1H); 7.3 (1H); 9.1 (1H) and ca. 11.4 (1H) ppm.

Example 26

1-Ethoxycarbonylmethyl-9-(3-trifluoroacetamidomethyl-1-pyrrolyl)5, 6,7,8-tetrahydrobenzo[f]quinoxaline-2,3(1H,4H)-dione

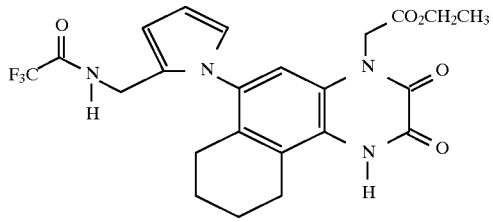

a) N-(5,6,7,8-Tetrahydro-1-napthyl)acetamide 100 ml (1.1 mol) of acetic anhydride were added dropwise to 100 ml (0.72 mol) of 5,6,7,8-tetrahydro-1-naphtylamine dissolved in 800 ml of tetrahydrofuran at room temperature. The mixture was then stirred at 40° C. for 1 h. After cooling, the product was precipitated by adding petroleum ether. 120 g (94%) of product were obtained.

$^1$-H-NMR (D$_6$-DMSO): δ=1.75 (4H); 2.1 (3H); 2.6 (2H); 2.8 (2H); 6.9 (1H); 7.1 (1H); 7.2 (1H) and 9.1 (1H) ppm.

b) N-(2,4-Dinitro-5,6,7,8-tetrahydro-1-naphthyl)acetamide 120 g (0.63 mol) of product 26a were dissolved in 1,200 ml of concentrated sulfuric acid. At 10° C., 80 ml of 98% strength nitric acid were added dropwise over the course of 2 h. The mixture was then stirred for 30 min and subsequently poured onto ice. The precipitate was filtered off with suction and recrystallized from ethanol. Yield: 86 g (49%); melting point 203° C.

$^1$H-NMR (D$_6$-DMSO): δ=1.8 (4H); 2.1 (3H); 2.8 (2H); 3.0 (2H); 8.4 (1H) and 10.1 (1H) ppm.

c) 2,4-Dinitro-5,6,7,8-tetrahydro-1-naphthylamine 80 g (0.29 mol) of product 26b were refluxed in a mixture of 250 ml of ethanol, 250 ml of concentrated hydrochloric acid and 100 ml of water for 3 h. The precipitate was then filtered off with suction. 55 g (85%) of product were obtained, melting point 175°–176° C.

$^1$H-NMR (D$_6$-DMSO): δ=1.7 (2H); 1.9 (2H); 2.5 (2H); 3.0 (2H); 7.9 (2H, NH$_2$) and 8.6 (1H) ppm.

d) 2-Amino-4-nitro-5,6,7,8-tetrahydro-1-napthylamine 123 g (3.1 mol) of sodium hydroxide solution and 123 g (0.48 mol) of sulfur were heated [lacuna] 1 l of water at 100° C. until the solution clarified (about 1 h). Then 1 l of methanol and, in portions, 54 g (0.23 mol) of product 26c were added. The mixture was then stirred for 30 min. The methanol was removed under reduced pressure, and the aqueous phase was cooled with ice. The resulting precipitate was filtered off with suction. 34 g (73%) of product were obtained, melting point 181°–182° C.

$^1$H-NMR (D$_6$-DMSO): δ=1.7 (2H); 1.8 (2H); 2.4 (2H); 2.9 (2H); 4.9 (2H); 5.6 (2H) and 7.3 (1H) ppm.

e) 9-Nitro-5,6,7,8-tetrahydrobenzo[f]quinoxaline-2,3(1H, 4H)-dione 33.5 g (0.16 mol) of product 26d were refluxed in 300 ml of diethyl oxalate for 3 h. The precipitate was then filtered off with suction. 29.7 g (71%) of product were obtained, melting point >250° C.

$^1$H-NMR (D$_6$-DMSO): δ=1.6–1.9 (4H); 2.8 (2H); 2.9 (2H); 7.6 (1H); 11.4 (1H) and ca. 12 (broad) ppm.

f) 1-Ethoxycarbonylmethyl-9-nitro-5,6,7,8-tetrahydrobenzo[f]quinoxaline-2,3(1H,4H)-dione 29 g (0.11 mol) of product 26e were dissolved under protective gas in 300 ml of dimethylformamide and, at room temperature, 3.3 g (0.11 mol) of sodium hydride (80%) were added in portions. The mixture was subsequently stirred for 1 h. Then 12.9 ml (0.12 mol) of ethyl bromoacetate were rapidly added dropwise, and the mixture was stirred at room temperature for 2 h. Subsequently 50 ml of acetic acid were added dropwise, and the mixture was concentrated under reduced pressure. The residue was purified by chromatography (mobile phase=toluene:acetone:glacial acetic acid =40:20:1). 12.5 g (33%) of product were obtained, melting point 217°–219° C.

$^1$H-NMR (D$_6$-DMSO): δ=1.2 (3H); 1.7 (2H); 1.8 (2H); 2.8 (2H); 2.9 (2H); 4.2 (2H); 5.0 (2H); 7.8 (1H) and 11.5 (1H) ppm.

g) 9-Amino-1-ethoxycarbonylmethyl-5,6,7,8-tetrahydrobenzo[f]quinoxaline-2,3(1H,4H)-dione 5 g (14.4 mmol) of product 26f were dissolved in 150 ml of dimethylformamide and hydrogenated after addition of 0.5 g of palladium/carbon (10%). The mixture was then filtered, and the filtrate was concentrated under reduced pressure. 3.9 g (87%) of product-were obtained, melting point >250° C.

$^1$H-NMR (D$_6$-DMSO): δ=1.2 (3H); 1.8 (4H); 2.4 (2H); 2.7 (2H); 4.2 (2H); 4.9 (4H); 6.4 (1H) and 10.9 (1H) ppm.

h) 1-Ethoxycarbonylmethyl-9-(3-trifluoroacetamidomethyl1-pyrrolyl)-5, 6,7,8-tetrahydrobenzo[f]quinoxaline-15 2,3(1H,4H)-dione 3.5 g (11.0 mmol) of product 26 g and 3.5 g (13.8 mmol) of product 4a were refluxed in 100 ml of concentrated acetic acid for 10 min. The mixture was then concentrated under reduced pressure, and the residue was treated with a little ethanol. The precipitate was filtered off with suction. 4.4 g (82%) of product were obtained, melting point 242°–243° C.

$^1$H-NMR (D$_6$-DMSO): δ=1.2 (3H); 1.6 (2H); 1.8 (2H), 2.4 (2H); 2.8 (2H); 4.2 (2H); 4.3 (2H); 5.0 (2H); 6.2 (1H); 6.8 (2H);

7.1 (1H); 9.8 (1H) and 11.4 (1H) ppm.

Example 27

9-(3-Aminomethyl-1-pyrrolyl)-1-carboxymethyl-5,6,7,8-tetrahydrobenzo[f]quinoxaline-2,3(1H,4H)-dione

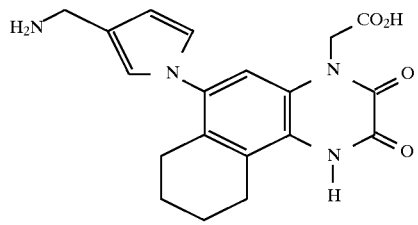

4.3 g (8.7 mmol) of Example 26 were suspended in 20 ml of tetrahydrofuran, and 0.84 g (35.1 mmol) of lithium hydroxide dissolved in 50 ml of water was added. The mixture was stirred at room temperature for 1 h, then the tetrahydrofuran was removed under reduced pressure, and the resulting aqueous phase was neutralized with 1M hydrochloric acid. The precipitate was filtered off with suction. 2.3 g (72%) of product were obtained, melting point >250° C.

$^1$H-NMR (CD$_3$COOD): δ=1.7 (2H), 1.9 (2H); 2.5 (2H); 2.9 (2H); 4.2 (2H); 5.1 (2H); 6.4 (1H); 6.8 (1H); 7.0 (1H); and 7.1 (1H) ppm.

Example 28

N-(1-(1-Carboxymethyl-5,6,7,8-tetrahydrobenzo[f]quinoxaline-2,3(1H,4H)-dion-9-yl)-3-pyrrolyl)methyl-N'-phenylurea

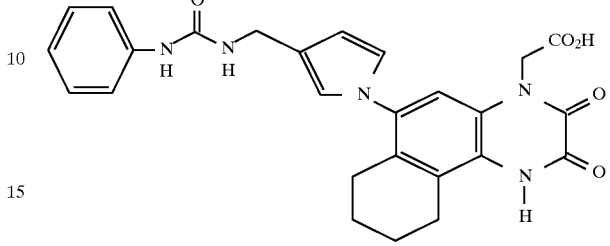

0.7 g (1.9 mmol) of the substance from Example 27 and 0.24 g (2.0 mmol) of phenyl isocyanate were heated in 5 ml of anhydrous dimethylformamide at 110° C. for 15 min. After cooling, the product was precipitated by adding ether. 0.86 g (97%) of product was obtained, melting point 198° C. (decomposition).

$^1$H-NMR (D$_6$-DMSO): δ=1.7 (2H); 1.8 (2H); 2.5 (2H); 2.8 (2H); 4.2 (2H); 5.0 (2H); 6.2 (1H); 6.3 (1H); 6.8 (2H); 6.9 (1H); 7.1 (1H) 7.3 (2H); 7.4 (2H); 8.5 (1H); 11.4 (1H) and ca. 13.5 (broad) ppm.

Example 29

N-(1-(1-Carboxymethyl-5,6,7,8-tetrahydrobenzo[f]quinoxaline-30 2,3(1H,4H)-dion-9-yl)-3-pyrrolylmethyl-N'-(4-nitrophenyl)urea [sic]

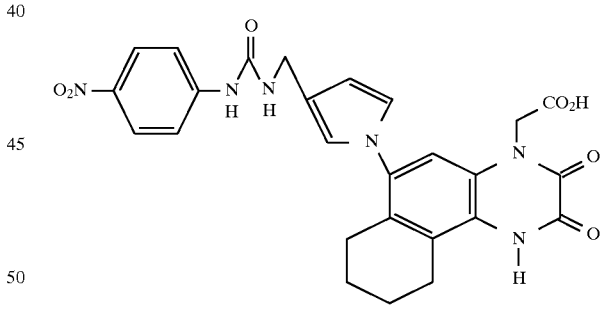

0.4 g (2.2 mmol) of the substance from Example 27 and 0.38 g (2.3 mmol) of 4-nitrophenyl isocyanate were heated in 5 ml of anhydrous dimethylformamide at 120° C. for 10 min. Then a further 0.38 g of 4-nitrophenyl isocyanate was added. After a further 5 min, the mixture was cooled and filtered. Methylene chloride was added to the filtrate, whereupon the product precipitated. 0.75 g (66%) was obtained, melting point >180° C.

$^1$H-NMR (D$_6$-DMSO): δ=1.6 (2H); 1.8 (2H); 2.4 (2H); 2.9 (2H); 4.2 (2H); 4.9 (2H); 6.2 (1H); 6.8 (3H); 7.1 (1H); 7.6 (2H); 8.2 (2H) 9.3 (1H); 11.3 (1H) and ca. 13 (broad) ppm.

Example 30

N-(1-(1-Hydroxy-5,6,7,8-tetrahydrobenzo[f]
quinoxaline-2,3(1H,4H)-dion-9-yl)-3-pyrrolyl)
methyl-N'-(4-nitrophenyl)urea

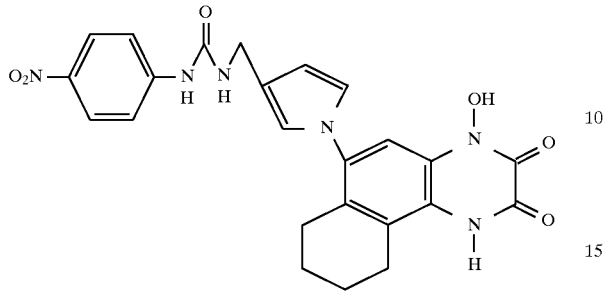

a) N-(2,5-Dimethoxy-3-tetrahydrofuranyl)methyl-N'-(4-nitrophenyl)urea 25 g (0.15 mol) of 4-nitrophenyl isocyanate were added dropwise to a solution of 27 g (0.18 mol) of 3-aminomethyl2,5-dimethoxytetrahydrofuran in 150 ml of methylene chloride at 0°–5° C. After warming to room temperature, the resulting precipitate was filtered off with suction. 45 g of a crude product were obtained and were used without purification.

b) N-(1-(1-Hydroxy-5,6,7,8-tetrahydrobenzo[f]quinoxaline-2,3(1H,4H)-dion-9-yl)-3-pyrrolyl)methyl-N'-(4-nitrophenyl)urea [sic]

2.0 g (8 mmol) of product 1c and 3.3 g (10 mmol) of product 30a were reacted by method 1d. 1.3 g (33%) of product were obtained, melting point >230° C.

$^1$H-NMR (D$_6$-DMSO): δ=1.5–1.9 (4H); 2.4 (2H); 2.8 (2H); 4.2 (2H); 6.2 (1H); 6.7 (1H); 6.8 (2H); 7.1 (1H); 7.7 (2H); 8.2 (2H); 9.4 (1H) and ca. 11.5 (broad) ppm.

Example 31

N'-(4-Nitrophenyl)-N-(1-(5,6,7,8-tetrahydrobenzo[f]
quinoxaline-2,3(1H,4H)-dione-9-yl)-3-pyrrolyl)
methylurea

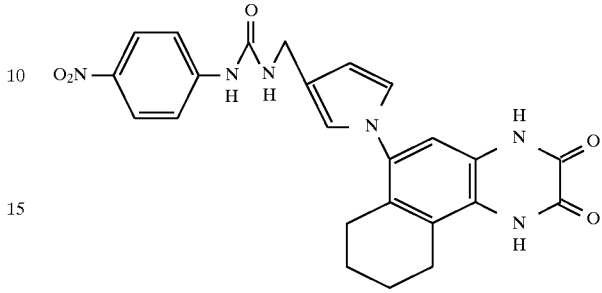

9.3 g (40 mmol) of product 12a and 13 g (40 mmol) of product 30a were reacted by method Id. Yield: 17.1 g (90%), melting point: 239° C.

$^1$H-NMR (D$_6$-DMSO): δ=1.6–1.9 (4H); 2.5–3.0 (4H); 4.2 (2H); 6.2 (1H); 6.6 (1H); 6.7 (2H); 7.3–8.3 (5H); 9.2 (1H); 11.1 (1H) and 12 (broad) ppm.

Example 32

N-(1-(1-Ethoxycarbonylmethyl-5,6,7,8-tetrahydrobenzo[f]quinoxaline-2,3(1H,4H)-dion-9-yl)-3-pyrrolyl)methyl-N'-(4-nitrophenyl)urea

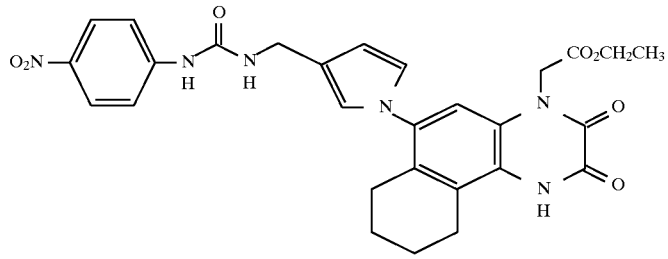

16.6 g (35 mmol) of product 31 and 5.9 g (35 mmol) of ethyl bromoacetate were reacted at room temperature as in Example 20. The product was additionally purified by chromatography on silica gel (mobile phase: toluene/acetone/acetic acid =20/10/1). Yield: 4 g (21%); melting point 246° C.

$^1$H-NMR (D$_6$-DMSO9 [sic]: δ=1.2 (3H); 1.6–2.0 (4H); 2.4 (2H); 2.8 (2H); 4.2 (2H); 5.0 (2H); 6.2 (1H); 6.7 (1H); 6.8 (2H); 7.2 (1H); 7.5–8.3 (4H); 9.2 (1H) and ca. 11.3 (broad) ppm.

Example 33

9-(2-Acetamidomethyl-1-pyrrolyl)-1-hydroxy-5,6,7,8-tetrahydroenzo[f]quinoxaline-2,3(1H,4H)-dione

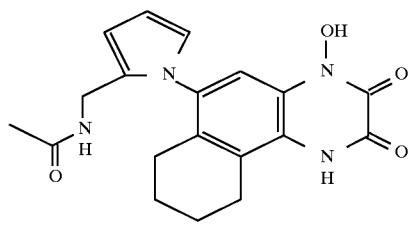

4.4 g (18 mmol) of product 1c and 4.5 g (22 mmol) of product 25e were reacted by method 1d. Yield: 2.9 g (44%), melting point 295° C. (decomposition).

$^1$H-NMR (D$_6$-DMSO): δ=1.6–1.9 (7H); 2.2 (2H); 2.9 (2H); 3.9 (2H) 6.1 (2H); 6.7 (1H); 7.2 (1H); 8.0 (1H) and ca. 11.5 (broad) ppm.

Example 34

1-Hydroxy-9-(3-(4-(4-nitrophenyl)-1-piperazinyl)methyl-1-pyrrolyl)-5,6,7,8-tetrahydrobenzo[f]quinoxaline-2,3(1H,4H)-dione

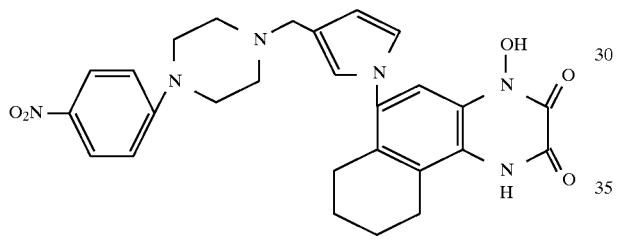

2 g (6 mmol) of product 1 and 2.5 g (12 mmol) of 4-(4-nitrophenyl)piperazine were reacted by method 14. Yield: 2.7 g (86%), melting point >230° C.

$^1$H-NMR (D$_6$-DMSO): δ=1.6 (2H); 1.8 (2H); 2.4 (2H); 2.8 (2H); 3.3–3.7 (9H); 6.1 (1H); 6.7 (1H); 6.8 (1H); 7.0 (2H); 7.2 (1H); 8.0 (2H) and ca. 11.5 (broad) ppm.

Example 35

N-(1-(1-Carboxymethyl-5,6,7,8-tetrahydrobenzo[f]quinoxaline-2,3(1H,4H)-dion-9-yl)-3-pyrrolyl)methyl-N'-phenylguanidine

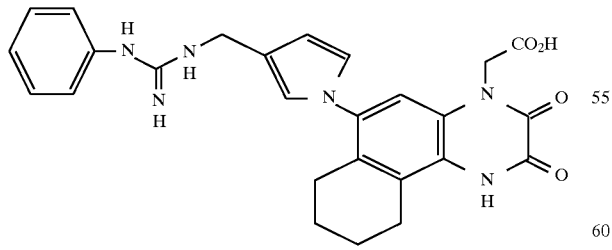

1.75g (4.8 mmol) of product 27, 1.4 g (4.8 mmol) of S-methyl-N-phenylisothiourea hydroiodide and a spatular tip of 4-(N,N-di-methylamino)pyridine were refluxed in 50 ml of pyridine for 6 h. The mixture was then poured into water and acidified with dilute hydrochloric acid, and the resulting precipitate was filtered off with suction. 0.96 g (42%) of product were obtained, melting point >225° C.

Example 36

N-(1-(1-Carboxymethyl-5,6,7,8-tetrahydrobenzo[f]quinoxaline-25 2,3(1H,4H)-dion-9-yl)-3-pyrrolyl)methyl-N,-(4-nitrophenyl)guanidine

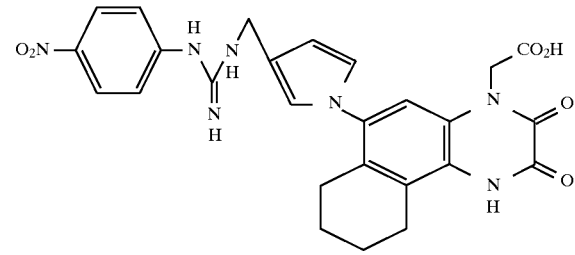

1.8 g (4.8 mmol) of product 27 and 1.6 g (4.8 mmol) of S-methyl-N-(4-nitrophenyl)isothiourea hydroiodide were reacted by method 35. Yield: 1.4 g (54%), melting point >240° C.

$^1$H-NMR (D$_6$-DMSO): δ=1.5 (2H); 1.7 (2h [sic]); 2.3 (2H); 2.7 (2H); 4.3 (2H); 4.7 (2H); 6.2 (1H); 6.7 (1H); 6.8–7.0 (2H); (2H); 8.2 (2H); 8.4 (broad); 9.5 (broad) and ca. 11.2 (broad) ppm.

Example 37

N-(1-(1-Hydroxy-5,6,7,8-tetrahydrobenzo[f]quinoxaline-2,3(1H,4H)-dion-9-yl)-3-pyrrolyl)methyl-N,-(4-trifluoromethylphenyl)urea

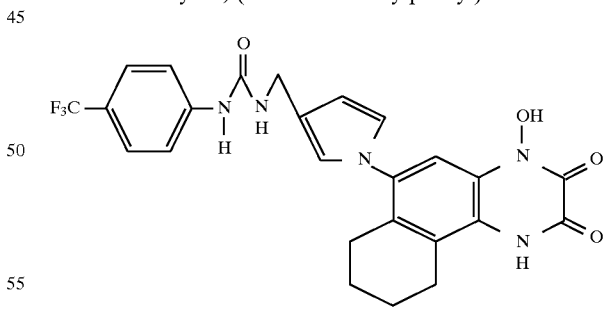

1.5 g (4.5 mmol) of product 5 and 0.9 g (4.7 mmol) of 4-trifluoromethylphenyl isocyanate were reacted as in Example 6. Yield: 2.1 g (91%), melting point: >215° C.

$^1$H-NMR (D$_6$-DMSO): δ=1.5 (2H); 1.7 (2H); 2.4 (2H); 2.7 (2H); 4.1 (2H); 6.1 (1H); 6.6 (1H); 6.8 (2H); 7.1 (1H); 7.5–7.7 (4H); 9.0 (1H) and ca. 11.3 (broad) ppm.

Example 38

N-(1-(1-Carboxymethyl-5,6,7,8-tetrahydrobenzo[f]
quinoxaline-25 2,3(1H,4H)-dion-9-yl)-3-pyrrolyl)
methyl-N'-(4-trifluoromethylphenyl)urea

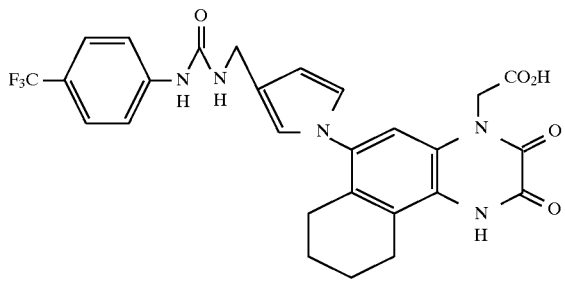

1.3 g (3.5 mmol) of product 27 and 0.68 g (3.7 mmol) of 4-trifluoromethylphenyl isocyanate were reacted as in Example 6. Yield: 1.4 g (72%), melting point >210° C.

$^1$H-NMR (D$_6$-DMSO): δ=1.5 (2H); 1.7 (2H); 2.4 (2H); 2.7 (2H); 4.1 (2H); 4.7 (2H); 6.1 (1H); 6.7 (3H); 6.9 (1H); 7.4–7.6 (4H); (1H); 10.7 (1H) and 11.2 (broad) ppm.

Example 39

1-Ethoxycarbonylmethyl-9-(3-(4-(4-nitrophenyl)-1-piperazinyl)1-pyrrolyl)-5, 6,7,8-tetrahydrobenzo[f]quinoxaline-2,3(1H,4H)-dione

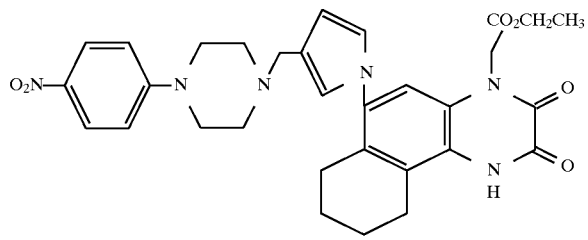

1.24 g (3.1 mmol) of product 20 and 1.3 g (6.3 mmol) of 4-nitrophenylpiperazine were reacted as in Example 14. Yield: 1.1 g (59%), melting point 229° C.

$^1$H-NMR (D$_6$-DMSO): δ=1.2 (3H); 1.7 2H); 1.8 (2H); 2.4 (2H); 2.9 (2H); 3.3–3.7 (8H); 4.2 (2H); 5.0 (2H); 6.2 (1H); 6.8 (2H), 7.0 (2H); 7.1 (1H), 8.0 (2H) and ca. 11.5 (1H) ppm.

Example 40

9-(3-Carboxy-1-pyrrolyl)-1-ethoxycarbonylmethyl-5,6,7,8-tetrahydrobenzo[f]quinoxaline-2,3(1H,4H)-dione

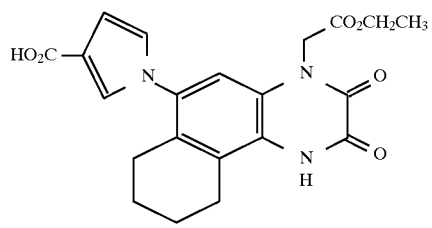

0.52 g (1.3 mmol) of product 20 and 0.49 g (1.3 mmol) of dicyclohexano-18-crown-6 were dissolved in 20 ml of acetone and heated to reflux. Then 0.83 g (5.3 mmol) of potassium permanganate was added in portions, and boiling was continued for 30 min. 10 ml of water were added, and boiling was continued for 15 min. The mixture was then filtered and the precipitate was washed with dilute hydrochloric acid and ethyl acetate. The aqueous phases were diluted with water and extracted with ethyl acetate. The combined ethyl acetate phases were then extracted with aqueous sodium bicarbonate solution. The latter was acidified with hydrochloric acid and again extracted with ethyl acetate. This organic phase was then dried and concentrated under reduced pressure. Yield: 0.2 g (35%), melting point: 282° C.

$^1$H-NMR (D$_6$-DMSO): δ=1.2 (3H); 1.7 (2H); 1.8 (2H); 2.4 (2H); 2.8 (2H); 4.2 (2H); 5.0 (2H); 6.6 (1H), 6.9 (1H); 7.3 (1H); 7.4 (1H); 11.3 (1H) and ca. 13 (1H) ppm.

Example 41

1-Ethoxycarbonylmethoxy-9-(3-trifluoroacetamidomethyl1-pyrrolyl)-5,6,7,8-tetrahydrobenzo[f]quinoxaline-2,3(1H,4H)-dione

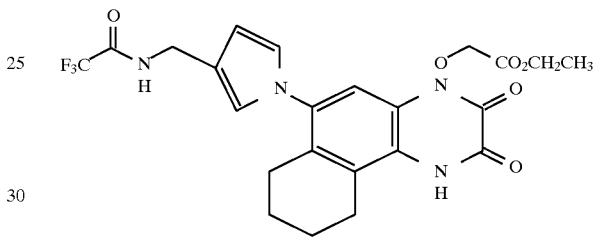

2.5 g (5.9 mmol) of product 4 and 1.5 g (8.9 mmol) of ethyl bromoacetate were reacted as in Example 8. Yield: 2.8 g (92%), melting point 199° C.

$^1$H-NMR (D$_6$-DMSO): δ=1.2 (3H); 1.7 (2H); 1.8 (2H); 2.4 (2H); 2.8 (2H), 4.2 (2H); 4.3 (2H); 5.0 (2H); 6.2 (1H); 6.9 (2H); 7.3 (1H) 9.8 (1H) and 11.3 (1H) ppm.

Example 42

1-Ethoxycarbonylmethyl-9-(3-(4-nitrobenzylcarbamoyl)-1-pyrrolyl)-5,6,7,8-tetrahydrobenzo[f]quinoxaline-2,3(1H,4H)-dione

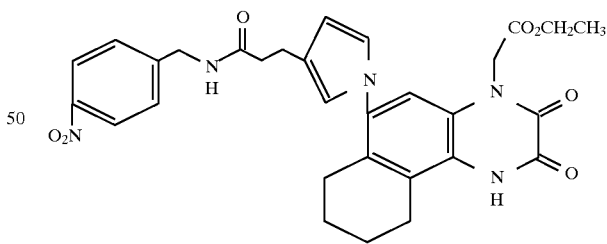

1.5 g (3.6 mmol) of the substance from Example 40 were dissolved in 50 ml of anhydrous dimethylformamide and, at room temperature, 0.73 g (4.5 mmol) of carbonyldiimidazole was added. The mixture was stirred at room temperature for 30 min and at 50° C. for a further 30 min. Then 1.1 g (7.3 mmol) of 4-hitrobenzylamine were added, and the mixture was stirred at 80° C. for 1 h. The solvent was then removed under reduced pressure, and the residue was treated with dilute hydrochloric acid. The resulting solid was filtered off with suction. 1.5 g (74%) of product were obtained, melting point 165° C.

$^1$H-NMR (D$_6$-DMSO): δ=1.2 (3H), 1.6 (2H); 1.8 (2H); 2.4 (2H); 2.8 (2H), 4.1 (2H); 4.5 (2H); 5.0 (2H); 6.7 (1H); 6.9 (2H); 7.2 (1H) 7.4–7.7 (3H), 8.1–8.3 (2H); 8.6 (1H) and 10.8 (1H) ppm.

Example 43

9-(3-Aminomethyl-1-pyrrolyl)-1-carboxymethyloxy-5,6,7,8-tetrahydrobenzo[f]quinoxaline-2,3(1H,4H)-dione

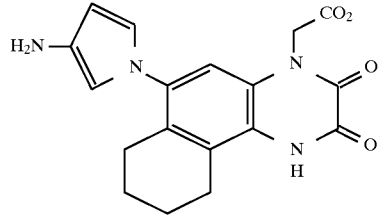

2.1 g (4.2 mmol) of the substance from Example 41 were reacted with 0.5 g (21 mmol) of lithium hydroxide as in Example 10. 1.4 g (85%) of product were obtained, melting point >300° C.

$^1$H-NMR (D$_6$-DMSO): δ=1.6 (2H), 1.75 (2H); 2.4 (2H); 2.7 (2H), 3.8 (2H); 4.3 (2H); 6.3 (1H); 6.8 (1H); 7.0 (1H); 7.5 (1H); 8.5 (broad) and 10.7 (1H) ppm.

Example 44

1-Carboxymethyl-9-(3-(4-(4-nitrophenyl)-1-piperazinyl)methyl-1-pyrrolyl)-5, 6,7,8-tetrahydrobenzo[f]quinoxaline-2,3(1H,4H)-dione

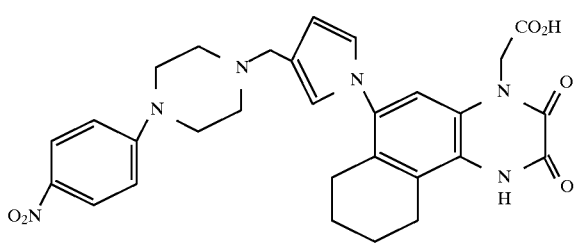

1 g (1.7 mmol) of the substance from Example 39 was reacted with 0.12 g (5.1 mmol) of lithium hydroxide as in Example 10. 0.9 g (95%) of product was obtained, melting point >300° C.

$^1$H-NMR (D$_6$-DMSO): δ1.6 (2H), 1.8 (2H); 2.4 (2H); 2.8 (2H), 3.0–4.0 (8H); 4.1 (2H); 4.9 (2H); 6.4 (1H); 6.9 (1H); 7.0–7.2 (3H); 8.1 (2H) and 10.8 (1H) ppm.

Example 45

1-Carboxymethyl-9-(4-(4-nitrobenzylcarbamoyl)-1-pyrrolyl)-5, 6,7,8-tetrahydrobenzo[f]quinoxaline-2,3 (1H,4H)-dione

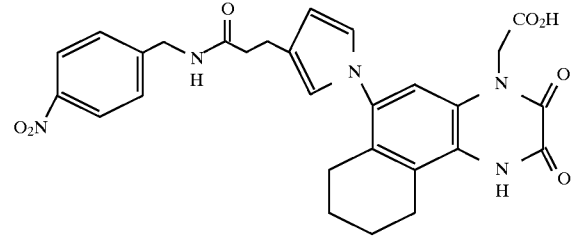

0.9 g (1.6 mmol) of the substance from Example 42 was reacted with 0.12 g (4.9 mmol) of lithium hydroxide as in Example 10. 0.7 g (81%) of product was obtained, melting point >220° C. (decomposition).

$^1$H-NMR (D$_6$-DMSO): δ=1.6 (2H); 1.8 (2H); 2.4 (2H); 2.8 (2H), 4.6 (2H); 4.9 (2H); 6.7 (1H); 6.9 (2H); 7.2 (1H); 7.4 (1H), 7.6 (2H); 8.2 (2H); 8.6 (1H), 11.3 (1H) and ca. 13 (broad) ppm.

Example 46

1-Carboxymethyl-9-(3-carboxy-1-pyrrolyl)-5,6,7,8-tetrahydrobenzo[f]quinoxaline-2,3(1H,4H)-dione

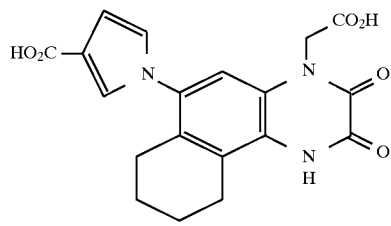

1.8 g (4.3 mmol) of the substance from Example 40 and 0.41 g (17.2 mmol) of lithium hydroxide were reacted as in Example 10. 1.3 g (80%) of product were obtained, melting point >245° C. (decomposition).

$^1$H-NMR (D$_6$-DMSO): δ=1.6 (2H); 1.8 (2H); 2.4 (2H); 2.8 (2H), 4.9 (2H); 6.6 (1H); 6.9 (1H); 7.2 (1H); 7.4 (1H), 11.3 (1H) and ca. 12.5 (broad) ppm.

Example 47

N-(1-(1-Carboxymethyl-5,6,7,8-tetrahydrobenzo[f]quinoxaline-2,3(1H,4H)-dion-9-yl)-3-pyrrolylmethyl)-N'-(3-ethoxycarbonyl-phenyl)urea

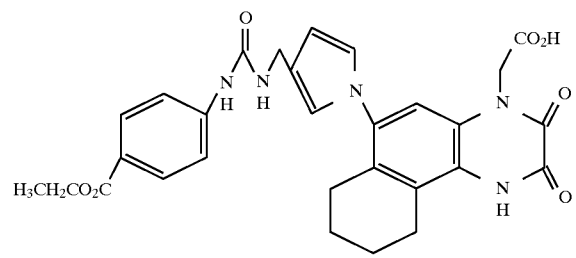

2.0 g (5 mmol) of the substance from Example 27 and 1.1 g (5.5 mmol) of 3-ethoxycarbonylphenyl isocyanate were reacted as in Example 29. 1.4 g (50%) of product were obtained, melting point >200° C. (decomposition).

¹H-NMR (D₆-DMSO): δ=1.3 (3H); 1.6 (2H); 1.8 (2H); 2.45 (2H), 2.8 (2H); 4.2 (2H); 4.3 (2H); 4.9 (2H); 6.2 (1H); 6.3 (1H), 6.8 (2H); 7.0 (2H); 7.4 (1H); 7.5 (1H); 7.6 (1H); 8.1 (1H); 8.7 (1H); 11.3 (1H) and ca. 13.2 (broad) ppm.

Example 48

1-Ethoxycarbonylmethyl-9-(2-trifluoroacetamidomethyl-1-pyrrolyl)-5, 6,7,8-benzo[f]quinoxaline-2,3(1H,4H)-dione [sic]

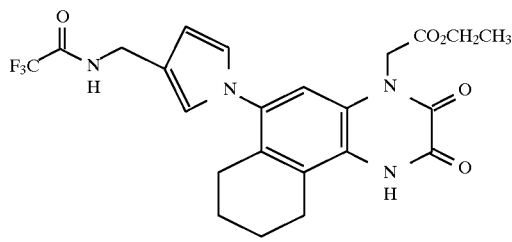

a) (N-((2,5-Dimethoxy-2-tetrahydrofuranyl)methyl)trifluoroacetamide 25.0 g (155 mmol) of 2-aminomethyl-2,5-dimethoxytetrahydrofuran, 15.7 g (155 mmol) of triethylamine and 1 spatula tip of 4-(N,N-dimethylamino)pyridine were dissolved in 200 ml of ether. At 0°–5° C., 32.6 g (155 mmol) of trifluoroacetic anhydride were added dropwise. The mixture was stirred for 1 h. The ether phase was then washed with water, dried and concentrated under reduced pressure. 32 g (80%) of a crude product were obtained and were used further as such.

b) 1-Ethoxycarbonylmethyl-9-(2-trifluoroacetamidomethyl-1-pyrrolyl)-5, 6,7,8-benzo[f]quinoxaline-2,3(1H,4H)-dione 1.5 g (4.7 mmol) of the substance from Example [lacuna] and 1.5 g (5.9 mmol) of the product obtained in a) were reacted as in Example 1d. 1.8 g (75%) of product were obtained, melting point >120° C. (decomposition).

¹H-NMR (D₆-DMSO): δ=1.2 (3H); 1.5 (1H); 1.65 (1H); 1.7 (1H), 1.8 (1H); 2.1 (1H); 2.3 (1H); 2.7–2.9 (2H); 4.0 (1H), 4.1 (3H) 5.0 (2H); 6.2 (2H); 6.7 (1H), 7.3 (1H); 9.5 (1H) and 11.3 (1H) ppm.

Example 49

N-(1-(1-Carboxymethyloxy-5,6,7,8-tetrahydrobenzo[f]quinoxaline-2,3(1H,4H)-dion-9-yl)-3-pyrrolylmethyl)-N'-(4-nitrophenyl)urea

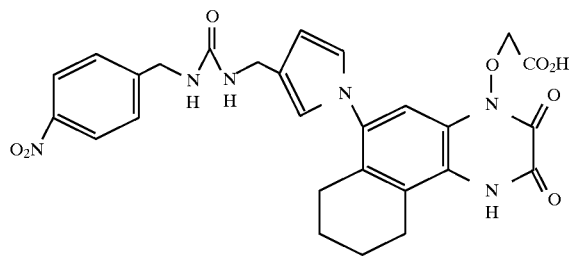

1.0 g (2.5 mmol) of Example 43 and 0.45 g (2.75 mmol) of 4-nitrophenyl isocyanate were reacted as in Example 29.

0.4 g(32%) of product was obtained, melting point >215° C. (decomposition).

¹H-NMR (D₆-DMSO): δ=1.7 (2H); 1.9 (2H); 2.6 (2H); 2.9 (2H), 4.4 (2H); 5.0 (2H); 6.3 (1H); 6.8 (1H); 7.6 (3H), 7.7 (1H); 8.1 (2H) and 8.2 (1H) ppm.

Example 50

9-(3-Benzylcarbamoyl-1-pyrrolyl)-1-ethoxycarbonylmethyl5, 6,7,8-tetrahydrobenzo[f]quinoxaline-2,3(1H,4H)-dione

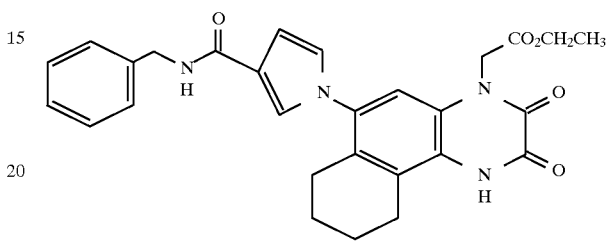

2.0 g (4.9 mmol) of the substance from Example 40 and 1.0 g (9.7 mmol) of benzylamine were reacted as in Example 42. 1.5 g (59%) of product were obtained, melting point >100° C. (decomposition).

¹H-NMR (D₆-DMSO): δ=1.2 (3H); 1.6 (2H); 1.8 (2H); 2.4 (2H), 2.8 (2H); 4.1 (2H); 4.4 (2H); 5.0 (2H); 6.7 (1H), 6.9 (1H); 7.1–7.5 (6H), 8.4 (1H) and ca. 11 (broad) ppm.

Example 51

1-Benzyloxy-9-(3-formyl-1-pyrrolyl)-5,6,7,8-tetrahydrobenzo[f]quinoxaline-2,3-dione

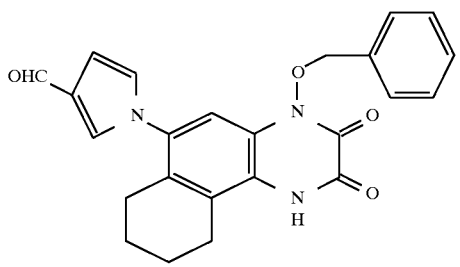

6.6 g (20 mmol) of Example 1 were reacted as in Example 8 with 5.2 g (30.6 mmol) of benzyl bromide. 8 g (94%) of product were obtained, melting point >230° C. (decomposition).

¹H-NMR (D₆-DMSO): δ=1.6 (2H); 1.8 (2H); 2.4 (2H), 2.8 (2H); 5.2 (2H); 6.6 (1H); 7.0 (1H); 7.1 (1H), 7.4 (1H); 7.6 (2H), 7.7 (1H); 9.8 (1H) and 11.4 (broad) ppm.

Example 52

N-(1-(1-Ethoxycarbonylmethyl-5,6,7,8-tetrahydrobenzo[f]quinoxaline-2,3-dion-9-yl)-3-pyrrolylmethyl)-N'-(4-ethoxycarbonylphenyl)urea

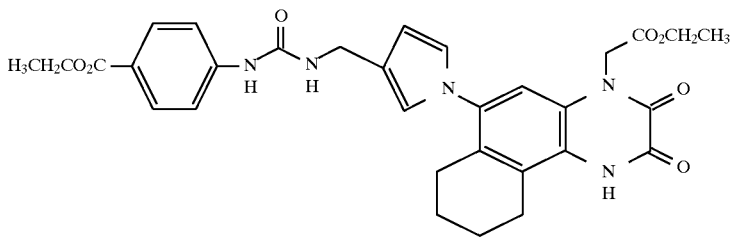

a) N'-(2,5-Dimethoxy-3-tetrahydrofuranyl)methyl-N-(4-ethoxycarbonyl)urea 25 g (0.16 mol) of 3-aminomethyl-2,5-dimethoxytetrahydrofuran (DE 26 45 234; CA 89, 24130) were dissolved in 200 ml of anhydrous tetrahydrofuran (DE 2,645,234; CA 89, 24130) were in 200 ml of anhydrous tetrahydorfuran [sic] and, at 0° C., 30 g (0.15 mol) of 4-ethoxycarbonylphenyl isocyanate dissolved in 100 ml of anhydrous tetrahydorfuran [sic] were added dropwise. After 30 min, the reaction mixture was concentrated under reduced pressure and used further without purification. 57 g were obtained.

b) N-(1-(1-Ethoxycarbonylmethyl-5,6,7,8-tetrahydrobenzo[f]quinoxaline-2,3-dion-9-yl)-3-pyrrolyl)methyl-N'-(4-ethoxycarbonylphenyl)urea 1.5 g (3.9 mmol) of the substance from Example 26 g and 1.2 g (4.3 mmol) of the substance obtained in a) were reacted as in 26 h. 1.1 g (40%) of product were obtained, melting point >160° C. (decomposition).

$^1$H-NMR (D$_6$-DMSO): δ=1.1–1.4 (6H); 1.6–1.8 (4H); 2.4 (2H); 2.8 (2H), 4.1–4.4 (6H); 5.0 (2H); 6.2 (1H); 6.5 (1H); 6.8 (2H), 7.1 (1H); 7.5 (2H), 7.6 (1H); 7.8 (2H), 8.9 (1H) and 11.3 (1H) ppm.

Example 53

N-[1-(1-Carboxymethyl-5,6,7,8-tetrahydrobenzo[f]quinoxaline-2,3-dion-9-yl)-3-pyrrolyl)methyl-N'-(3-carboxyphenyl)urea

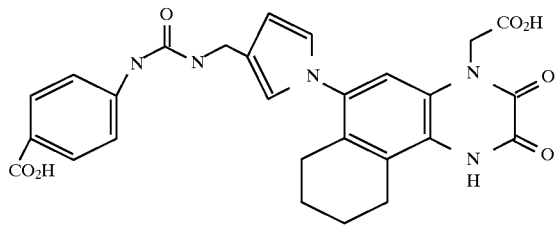

0.9 g (1.6 mmol) of the substance from Example 47 and 0.15 g (6.2 mmol) of lithium hydroxide were added as in Example 10. 0.7 g (87%) of product was obtained, melting point >210° C. (decomposition).

$^1$H-NMR (D$_6$-DMSO): δ=1.6 (3H); 1.8 (2H); 2.4 (2H), 2.8 (2H); 4.2 (2H); 4.9 (2H); 6.2 (2H); 6.4 (1H), 6.8 (1H); 7.0 (1H), 7.3 (1H), 7.5 (1H); 7.6 (1H); 8.1 (1H), 8.7 (1H) and 11.3 (broad) ppm.

Example 54

9-(2-Aminomethyl-1-pyrrolyl)-1-carboxymethyl-5,6,7,8-tetrahydrobenzo[f]quinoxaline-2,3(1H,4H)-dione

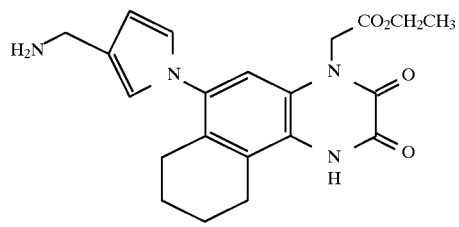

1.2 g (2.5 mmol) of Example 48 and 0.24 g (10 mmol) of lithium hydroxide were reacted as in Example 10. 0.7 g (86%) of product was obtained, melting point >285° C. (decomposition).

$^1$H-NMR (D$_6$-DMSO): δ=1.5–1.9 (4H); 2.0 (1H); 2.3 (1H), 2.8 (2H); 3.4+3.8 (2H); 4.5+4.8 (1H); 6.2 (1H); 6.4 (1H), 6.8 (1H) and 7.1 (1H) ppm.

Example 55

9-(3-Benzylcarbonyl-1-pyrrolyl)-1-carboxymethyl-5,6,7,8-tetrahydrobenzoa[f]quinoxaline-2,3(1H,4H)-dione

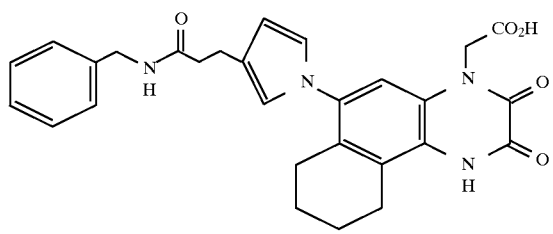

0.9 g (1.7 mmol) of Example 50 and 0.12 g (5.2 mmol) of lithium hydroxide were reacted as in Example 10. 0.7 g (81%) of product was obtained, melting point >200° C. (decomposition).

$^1$H-NMR (D$_6$-DMSO): δ=1.6 (2H); 1.8 (2H); 2.4 (2H), 2.8 (2H); 4.4 (2H); 4.9 (2H); 6.7 (1H); 6.9 (1H), 7.1–7.5 (6H); 8.4 (1H) and 7.1 (1H) ppm.

Example 56

1-Benzyloxy-9-(3-carboxy-1-pyrrolyl)-5,6,7,8-tetrahydrobenzo[f]quinoxaline-2,3(1H,4H)-dione

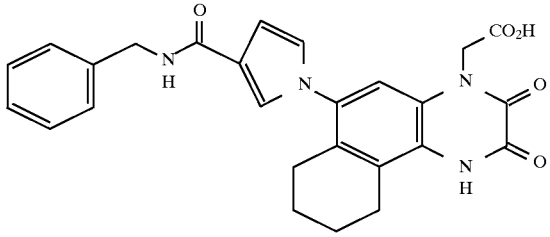

7.2 g (17 mmol) of Example 51 were oxidized as in Example 40 with 10.8 g (68 mmol) of potassium permanganate. 3.0 g (40%) of product were obtained, melting point >170° C. (decomposition).

$^1$H-NMR (D$_6$-DMSO): δ=1.6 (2H); 1.8 (2H); 2.4 (2H), 2.8 (2H); 5.2 (2H); 6.6 (1H); 6.9 (1H); 7.0 (1H), 7.4–7.6 (6H); 11.4 (1H) and ca. 12 (broad) ppm.

Example 57

9-(3-Carboxy-1-pyrrolyl)-1-hydroxy-5,6,7,8-tetrahydrobenzo[f]quinoxaline-2,3(1H,4H)-dione

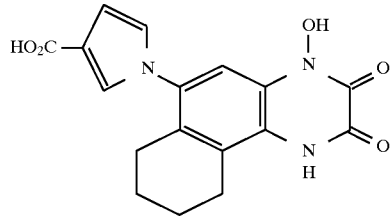

2.6 [lacuna] (6.0 mmol) of the substance from Example 56 were dissolved in 100 ml of dimethylformamide and hydrogenated after addition of 0.5 g of palladium/carbon (10%) with hydrogen. The mixture was then filtered, and the filtrate was concentrated under reduced pressure. The residue was treated with water, and the solid was filtered off with suction. 2.1 g (100%) of the product were obtained, melting point >300° C.

$^1$H-NMR (D$_6$-DMSO): δ=1.6 (2H); 1.8 (2H); 2.4 (2H), 2.8 (2H); 6.6 (1H); 6.9 (1H); 7.2 (1H), 7.5 (1H); 11.4 (1H), 11.8 (broad) and 1.02 (broad) ppm.

Example 58

N'-(4-Ethoxycarbonylphenyl)-N-(1-(1-hydroxy-5,6,7,8-tetrahydrobenzo[f]quinoxaline-2,3(1h,4H)-dion-9-yl)-3-pyrrolyl)methylurea

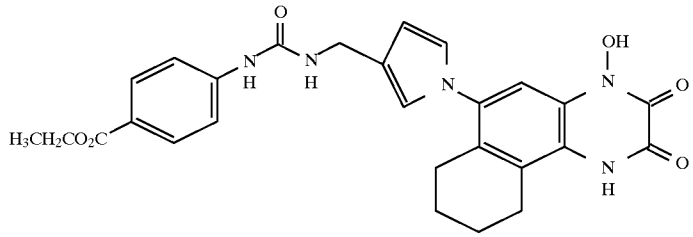

2.0 g (6 mmol) of the substance from Example 5 were reacted with 1.2 g (6 mmol) of 4-ethoxycarbonylphenyl isocyanate as in Example 6. 2.7 g (87%) of the product were obtained, melting point >220° C. (decomposition).

$^1$H-NMR (D$_6$-DMSO): δ=1.3 (3H); 1.6 (2H); 1.8 (2H), 2.4 (2H); 2.8 (2H); 4.2 (2H); 4.3 (2H); 6.2 (1H); 6.6 (1H), 6.8 (2H); 7.2 (1H); 7.5 (2H); 7.8 (2H) and 9.0 (1H) ppm.

Example 59

N'-(4-Carboxyphenyl)-N-(1-(1-hydroxy-5,6,7,8-tetrahydrobenzo[f]quinoxaline-2,3(1H,4H)-dion-9-yl)-3-pyrrolyl)methylurea

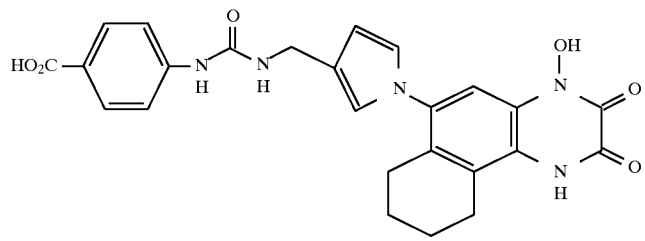

1.9 g (3,7 mmol) of the substance from Example 58 were reacted as in Example 10 with 0.44 g (18.4 mmol) of lithium hydroxide. 1.4 g (80%) of product were obtained, melting point >300° C.

$^1$H-NMR (D$_6$-DMSO): δ=1.6 (2H); 1.8 (2H), 2.45 (2H); 2.8 (2H); 4.2 (2H); 6.2 (1H); 6.5 (1H), 6.8 (2H); 7.1 (1H); 7.5 (2H); 7.8 (2H); 8.8 (1H); 11.3 (1H); 11.8 (broad) and 12.5 (broad) ppm.

Example 60

N-(1-(1-Carboxymethyl-5,6,7,8-tetrahydrobenzo[f]quinoxaline-2,3(1H,4H)-dion-9-yl)-3-pyrrolyl)methyl-N'-(4-carboxyphenyl)urea

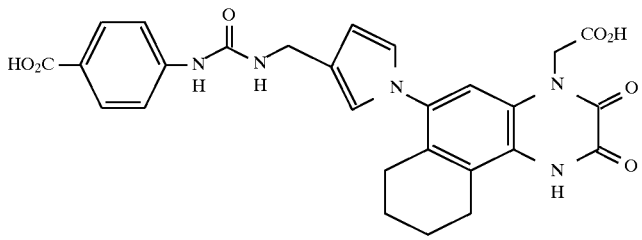

0.7 g (1.3 mmol) of the substance from Example 52 was reacted as in Example 10 with 0.15 g (6.3 mmol) of lithium hydroxide. 0.55 g (83%) of product was obtained, melting point >125° C. (decomposition).

$^1$H-NMR (D$_6$-DMSO): δ=1.3 (2H); 1.5–1.8 (3H); 2.3–2.9 (4H), 4.1–4.3 (2H); 4.7 (2H); 6.2 (1H); 6.7 (2H), 6.9 (1H); 7.4–7.9 (5H), 9.1 (1H), 11.1 (1H) and 11.3 (broad) ppm.

Example 61

1-Ethoxycarbonylmethyl-9-(3-(4-nitrophenylsulfonamidomethyl)-1-pyrrolyl)-5, 6,7,8-tetrahydrobenzo[f]quinoxaline-2,3(1H,4H)-dione

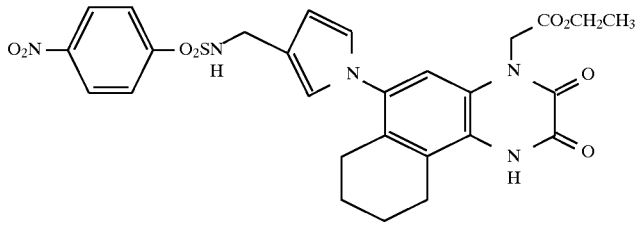

a) N-(2,5-Dimethoxy-3-tetrahydrofuranyl)methyl-4-nitrophenylsulfonamide 16.2 g (0.1 mol) of 3-aminomethyl-2,5-dimethoxytetrahydrofuran and 28 ml (0.2 mol) of triethylamine were dissolved in 250 ml of anhydrous tetrahydrofuran. At 0° C., 22.2 g (0.1 mol) of 4-nitrobenzenesulfonyl chloride dissolved in 100 ml of tetrahydrofuran were added dropwise. After 30 min, the mixture was filtered and the filtrate was concentrated under reduced pressure. The residue was partitioned between ethyl acetate and water, and the organic phase was dried and concentrated under reduced pressure. The residue was reacted further without purification. 28.6 g of an oil were obtained.

b) 1-Ethoxycarbonylmethyl-9-(3-(4-nitrophenylsulfonamidomethyl)-1-pyrrolyl)-5, 6,7,8-tetrahydrobenzo[f]quinoxaline-2,3(1H,4H)-dione 2.0 g (6.3 mmol) of the substance from Example 26 g and 2.3 g of the product obtained in a) were reacted as in Example 1d. 2.7 g (73%) of product were obtained, melting point 218°–220° C.

$^1$H-NMR (D$_6$-DMSO): δ=1.2 (3H); 1.6 (2H); 1.8 (2H); 2.3 (2H); 2.8 (2H), 4.0 (2H); 4.1 (2H), 5.0 (2H), 6.1 (1H), 6.6 (2H), 7.0 (1H); 8.0 (2H); 8.4 (3H) and 11.3 (1H) ppm.

Example 62

9-(3-(4-Ethoxycarbonylbenzylcarbamoyl)-1-pyrrolyl)-1-hydroxy-5, 6,7,8-tetrahydrobenzo[f]quinoxaline-2,3(1H,4H)-dione

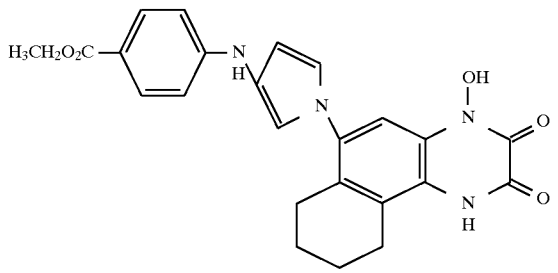

0.75 g (2.2 mmol) of the substance from Example 57 was reacted as in Example 42 with 0.6 g (2.2 mmol) of 4-ethoxycarbonylbenzylammonium bisulfate. 0.6 g (54%) of product was obtained, melting point >190° C. (decomposition).

$^1$H-NMR (D$_6$-DMSO): δ=1.3 (3H); 1.6 (2H); 1.8 (2H); 2.4 (2H); 2.7 (2H); 4.2–4.5 (4H); 6.7 (1H), 6.9 (1H), 6.9 (2H), 7.3–7.5 (3H), 7.9 (2H); 8.5 (1H) and ca. 10.7 (broad) ppm.

Example 63

1-Carboxymethyl-9-(3-(4-nitrophenylsulfonamidomethyl)-1-pyrrolyl)-5, 6,7,8-tetrahydrobenzo[f]quinoxaline-2,3(1H,4H)-dione

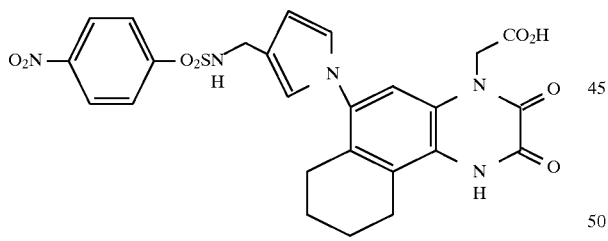

1.8 g (3 mmol) of the substance from Example 61 were reacted as in Example 10 with 0.37 g (16 mmol) of lithium hydroxide. 1.6 g (93%) of product were obtained, melting point >150° C. (decomposition).

$^1$H-NMR (D$_6$-DMSO): δ=1.5 (2H); 1.8 (2H); 2.3 (2H); 2.8 (2H), 4.0 (2H); 4.9 (2H), 6.0 (2H), 6.7 (2H), 6.9 (1H); 8.0–8.6 (6H) and 11.3 (1H) ppm.

We claim:
1. A pyrrolyltetrahydrobenzoquinoxalinedione of the formula I

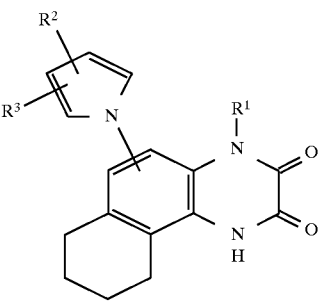

and its tautomeric forms, and its physiologically tolerated salts, in which the variables have the following meanings:

R$^1$ hydrogen; an aliphatic radical which has 1 to 6 carbon atoms and can carry one or two different substituents of the formulae —COOR$^4$, —CONHR$^4$, —CO—R$^4$, —OR$^4$, —NHR$^4$, —NH—CO—R$^4$, —CONHSO$_2$R$^4$ or NHSO$_2$R$^4$ where R$^4$ is hydrogen, C$_1$–C$_4$-alkyl, phenyl, benzyl, 1-phenylethyl or 2-phenylethyl, where the phenyl rings in R$^4$ can be substituted by 1, 2 or 3 of the following substituents: C$_1$–C$_4$-alkyl, CF$_3$, C$_1$–C$_4$-alkoxy, F$_3$CO—, halogen, nitro, CN, —OH, —CONHR$^5$ and/or —COOR$^5$ (R$^5$ hydrogen, C$_1$–C$_4$-alkyl, phenyl or benzyl);

—O—R$^6$ where R$^6$ can be hydrogen or an aliphatic radical which has up to 4 carbon atoms and can carry one of the following radicals: —COOR$^4$, —CONHR$^4$, —NHCOR$^4$, —NHSO$_2$R$^4$, —OH or phenyl, R$^2$ hydrogen, C$_1$–C$_4$-alkyl or phenyl, R$^3$ hydrogen or the radical —(CH$_2$)$_m$—R$^{7,}$ where m is 0, 1, 2, 3 or 4, and R$^7$ is hydrogen, C$_1$–C$_4$-alkyl, phenyl, phenylsulfonyl, NO$_2$, CN, —COO—(CH$_2$)$_n$—R$^8$, —CONHSO$_2$R$^4$, —CONH—(CH$_2$)$_n$—R$^8$, —CO—R$^8$, —CH=CH—CONHR$^8$, —CH=CH—COOR$^8$, —CH=NOR$^8$, —CH$_2$—NR$^8$R$^9$, CH$_2$NH—CY—(CH$_2$)$_n$R$^9$, CH$_2$NH—CY—X—(CH$_2$)$_n$—R$^9$, CH$_2$NH—CO—CF$_3$, CH$_2$NH—SO$_2$—R$^9$

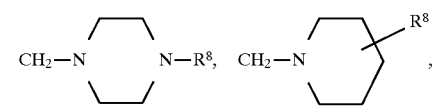

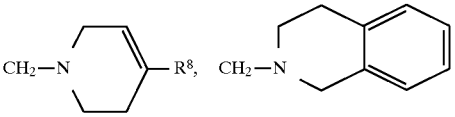

or

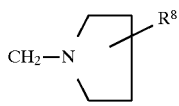

where X and Y are, independently of one another, oxygen or NH, n is 0, 1, 2, 3 or 4, R$^8$ is hydrogen or linear and branched C$_1$–C$_4$-alkyl which can be substituted by one or two phenyl or pyridyl radicals, and R$^9$ is hydrogen, linear or branched C$_1$–C$_6$-alkyl, phenyl or pyridyl, where all the phenyl or pyridyl radicals contained in R$^8$ and R$^9$ can carry one or two of the following radicals: O—C$_1$–C$_4$-alkyl, F, Cl, Br, I, C$_1$–C$_4$-alkyl, NO$_2$, CF$_3$, —COOR$^5$, —CONHR$^5$, NH$_2$, CN, —SO$_2$Ph, —NHSO$_2$R$^5$, —NHCOR$^5$, OH, —SO$_2$—C$_1$–C$_4$-alkyl, —NHCOCF$_3$, —SO$_2$R$^5$ and —OCF$_3$.

2. A method of treating Parkinson's disease, cerebral apoplectic insults, traumatic lesions of the brain and spinal cord, and epilepsy in a mammal suffering therefrom, which comprises administering to said mammal an effective amount of the compound of the formula I as defined in claim 1.

3. The method of claim 2, wherein the cerebral apoplectic insult is stroke.

4. A drug composition comprising the pyrrolyltetrahydrobenzoquinoxalinedione of formula I as defined in claim 1 and pharmaceutically acceptable excipients and diluents.

* * * * *